(12) United States Patent
Rush

(10) Patent No.: US 11,439,621 B2
(45) Date of Patent: Sep. 13, 2022

(54) METHOD OF TREATING STIMULANT USE DISORDER USING A COMBINATION OF TOPIRAMATE AND PHENTERMINE

(71) Applicant: University of Kentucky Research Foundation, Lexington, KY (US)

(72) Inventor: Craig R. Rush, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 47 days.

(21) Appl. No.: 16/889,320

(22) Filed: Jun. 1, 2020

(65) Prior Publication Data

US 2020/0375942 A1 Dec. 3, 2020

Related U.S. Application Data

(60) Provisional application No. 62/855,198, filed on May 31, 2019.

(51) Int. Cl.
*A61K 31/357* (2006.01)
*A61P 25/30* (2006.01)
*A61K 31/137* (2006.01)

(52) U.S. Cl.
CPC .......... *A61K 31/357* (2013.01); *A61K 31/137* (2013.01); *A61P 25/30* (2018.01)

(58) Field of Classification Search
CPC .................................................. A61K 31/357
USPC ......................................................... 514/455
See application file for complete search history.

(56) References Cited

PUBLICATIONS

Baldacara, J. Clin. Psychiatry 77, 398-406.*
Rothman, NeuroReport 8, 7-9 (1996).*
Glowa, Neuroreport 8, 1347-1351 (1197).*
Stafford, Behav. Pharmacol. 10, 775-784, 1999.*
Allison DB, Gadde KM, Garvey WT, Peterson CA, Schwiers ML, Najarian T, Tam PY, Troupin B, Day WW (2012). Controlled-release phentermine/topiramate in severely obese adults: a randomized controlled trial (EQUIP). Obesity, 20: 330-342.
Baldacara L, Cogo-Moreira H, Parreira BL, Diniz TA, Milhomem JJ, Fernandes CC, Lacerda AL (2016). Efficacy of topiramate in the treatment of crack cocaine dependence: a double-blind, randomized, placebo-controlled trial. J Clin Psychiatry, 77: 398-406.
Bray GA, Hollander P, Klein S, Kushner R, Levy B, Fitchet M, Perry BH (2003). A 6- month randomized, placebo-controlled, dose-ranging trial of topiramate for weight loss in obesity. Obes Res, 11: 722-733. Center for Disease Control and Prevention (2010). Obesity and Overweight, http://www.cdc.gov/nchs/fastats/overwt.htm. Accessed Nov. 17, 2010.
Gadde KM, Allison DB, Ryan DH, Peterson CA, Troupin B, Schwiers ML, Day WW (2011). Effects of low-dose, controlled-release, phentermine plus topiramate combination on weight and associated comorbidities in overweight and obese adults (CONQUER): a randomised, placebo-controlled, phase 3 trial. Lancet, 377:1341-1352.
Garvey WT, Ryan DH, Look M, Gadde KM, Allison DB, Peterson CA, Schwiers M, Day WW, Bowden CH (2012). Two-year sustained weight loss and metabolic benefits with controlled-release phentermine/topiramate in obese and overweight adults (SEQUEL): a randomized, placebo-controlled, phase 3 extension study. Am J Clin Nutr, 95: 297-308.
Johnson BA, Ait-Daoud N, Wang XQ, Penberthy JK, Javors MA, Seneviratne C and Liu L (2013b) Topiramate for the treatment of cocaine addiction: a randomized clinical trial. JAMA Psychiatry 70:1338-1346.
Johnson BA, Roache JD, Ait-Daoud N, Gunderson EW, Haughey HM, Wang XQ, Liu L (2012). Topiramate's effects on cocaine-induced subjective mood, craving and preference for money over drug taking. Addict Biol (ePub).
Kampman KM, Pettinati H, Lynch KG, Dackis C, Sparkman T, Weigley C, O'Brien CP (2004). A pilot trial of topiramate for the treatment of cocaine dependence. Drug Alcohol Depend, 75: 233-240.
Kampman KM, Pettinati HM, Lynch KG, Spratt K, Wierzbicki MR, O'Brien CP (2013). A double-blind, placebo-controlled trial of topiramate for the treatment of comorbid cocaine and alcohol dependence. Drug Alcohol Depend, 133: 94-99.
Kang JG, Park CY, Kang JH, Park YW, Park SW (2010). Randomized controlled trial to investigate the effects of a newly developed formulation of phentermine diffuse—controlled release for obesity. Diabetes Obes Metab, 12: 876-882.
Singh M, Keer D, Klimas J, Wood E, Werb D (2016). Topiramate for cocaine dependence: A systematic review and meta-analysis of randomized controlled trials. Addiction, 111: 1337-1346.
Stoops WW, Rush CR (2014). Combination pharmacotherapies for stimulant use disorder: a review of clinical findings and recommendations for future research. Expert Rev Clin Pharmacol, 7: 363-374.
Wang GJ, Volkow ND, Thanos PK, Fowler JS (2004). Similarity between obesity and drug addiction as assessed by neurofunctional imaging: A concept review. J Addict Dis, 23: 39-53.
Brauer, et al., Evaluation of Phentermine and Fenfluramine, Alone and in Combination, in Normal, Healthy Volunteers, \JecroPsychoPharmacology 1995—vol. 14, No. 4, pp. 233-241.

* cited by examiner

*Primary Examiner* — Nizal S Chandrakumar
(74) *Attorney, Agent, or Firm* — Stites & Harbison, PLLC; Mandy Wilson Decker; Gary N. Stewart

(57) ABSTRACT

Combinations and methods for treating a subject experiencing or at risk of experiencing an undesired consequence of stimulant use are provided. The combinations include topiramate and phentermine. The methods include administering an effective dose of a combination of topiramate and phentermine to a subject. In some embodiments, the methods include administering an effective dose of a combination of topiramate and phentermine to a subject with cocaine use disorder.

18 Claims, 8 Drawing Sheets

METHOD OF TREATING STIMULANT USE DISORDER USING A COMBINATION OF TOPIRAMATE AND PHENTERMINE

RELATED APPLICATIONS

This application claims the benefit of U.S. Provisional Application Ser. No. 62/855,198, filed May 31, 2019, the entire disclosure of which is incorporated herein by this reference.

GOVERNMENT INTEREST

This invention was made with government support under grant number RO1 DA036827 awarded by the National Institute on Drug Abuse (NIDA). The government has certain rights in the invention.

TECHNICAL FIELD

The present disclosure generally relates to combinations and methods for treating a subject who is experiencing or is at risk of experiencing an undesired consequence of stimulant use. In particular, the present disclosure relates to combinations and methods of treatment, which include topiramate and phentermine.

BACKGROUND

Use of, misuse of, abuse of, and/or addiction to stimulants, such as cocaine, methamphetamines, amphetamines, dextroamphetamines, and methylphenidates is an unrelenting public health concern. With respect to cocaine in particular, mortality rates from cocaine overdoses have doubled since 2013, and, in 2012, approximately 1.4 million Americans over the age of 12 years reported current cocaine use. Moreover, in 2009, primary cocaine abuse accounted for 9.3% of drug-abuse treatment admissions in the United States according to the Treatment Episode Data Set maintained by the Substance Abuse and Mental Health Services Administration (SAMHSA). Despite prevention and intervention efforts, cocaine abuse and dependence rates remain stable.

Behavioral therapies, such as contingency management and cognitive-behavioral therapy, are effective for reducing cocaine use and are currently considered the "standard of care" for cocaine use disorder. However, many patients enrolled in behavioral therapies are unable to achieve significant periods of abstinence, thus suggesting other strategies like pharmacotherapy are needed. Nonetheless, an effective medication has not been identified for cocaine use disorder, despite nearly four decades of research and the testing of at least 64 medications in more than 100 trials. Accordingly, there remains a need for medications and pharmacotherapy-based methods for treating individuals experiencing or at risk of experiencing unintended consequences (e.g., abuse or dependence) of stimulant use.

SUMMARY

The presently-disclosed subject matter meets some or all of the above-identified needs, as will become evident to those of ordinary skill in the art after a study of information provided in this document.

This summary describes several embodiments of the presently-disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this summary or not. To avoid excessive repetition, this summary does not list or suggest all possible combinations of such features.

The presently-disclosed subject matter includes combinations of topiramate and phentermine. The presently-disclosed subject matter further includes methods for treating a subject who is experiencing or is at risk of experiencing an undesired consequence of stimulant use. Such methods include administering an effect dose of a combination of topiramate and phentermine to a subject. In some embodiments, stimulant use includes stimulant misuse. Undesired consequences resulting from stimulant use include those which are consistent with characterizations of use or misuse of a stimulant, including abuse of or dependence on the stimulant. In some embodiments, the undesired consequence of stimulant use is the craving for administration of a stimulant. In some embodiments, the stimulant is cocaine. In this regard, methods for treating cocaine use disorder are also provided herein.

In some embodiments, the methods include administering the phentermine in a dose of about 15 mg/day. In other embodiments, the methods include administering the phentermine in a dose of more than about 15 mg/day. In other embodiments, the methods include administering the phentermine in a dose of about 15 mg/day to about 30 mg/day. In further embodiments, the methods include administering the phentermine in a dose of about 30 mg/day. In some embodiments, the methods include administering the topiramate in a dose of about 50 mg/day. In other embodiments, the methods include administering the topiramate in a dose of more than about 50 mg/day. In other embodiments, the methods include administering the topiramate in a dose of about 50 mg/day to about 100 mg/day. In further embodiments, the methods include administering the topiramate in a dose of about 100 mg/day. In some embodiments, the methods include administering the phentermine in a dose of about 15 mg/day and administering the topiramate in a dose of about 50 mg/day. In other embodiments, the methods include administering the phentermine in a dose of about 30 mg/day and administering the topiramate in a dose of about 50 mg/day. In other embodiments, the methods include administering the phentermine in a dose of about 15 mg/day and administering the topiramate in a dose of about 100 mg/day. In further embodiments, the methods include administering the phentermine in a dose of about 30 mg/day and administering the topiramate in a dose of about 100 mg/day.

Further features and advantages of the presently-disclosed subject matter will become evident to those of ordinary skill in the art after a study of the description, figures, and non-limiting examples in this document.

BRIEF DESCRIPTION OF THE DRAWINGS

The presently-disclosed subject matter will be better understood, and features, aspects and advantages other than those set forth above will become apparent when consideration is given to the following detailed description thereof. Such detailed description makes reference to the following drawings, wherein.

DESCRIPTION OF EXEMPLARY EMBODIMENTS

Figure 1A:
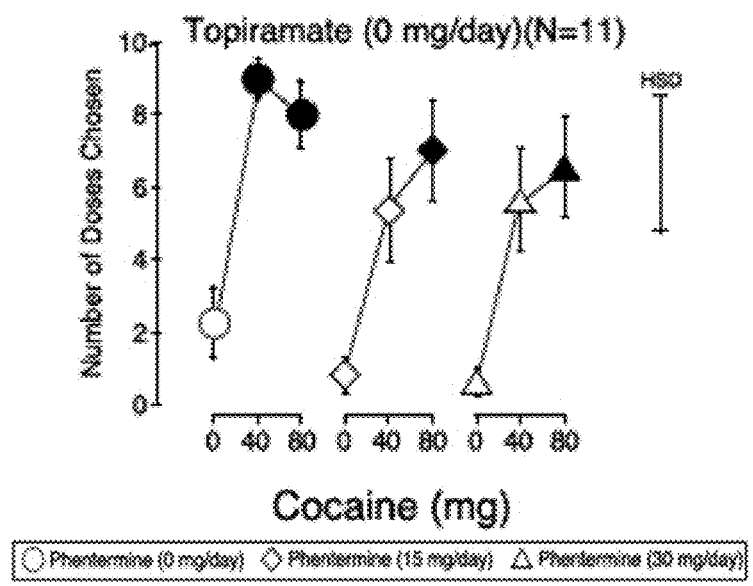
FIGS. 1A-C are graphs showing the results of cocaine self-administration of each topiramate group concurrently maintained on phentermine. (A) Mean (±SEM) Number of Drug Choices (maximum=10) on the Progressive-Ratio Procedure for cocaine (0, 40, 80 mg) during maintenance on topiramate (0 mg/day) and phentermine (0, 15, 30 mg/day); (B) topiramate (50 mg/day) and phentermine (0, 15, 30 mg/day); and (C) topiramate (100 mg/day) and phentermine (0, 15, 30 mg/day). Filled symbols indicate a significant difference from 0 mg cocaine during maintenance on 0 mg topiramate and 0 mg phentermine (far left circle). An asterisk (*) indicates a significant difference from maintenance on topiramate (0 mg/day) and phentermine (0 mg/day) at a given dose of cocaine (Tukey's Honestly Significant Difference (HSD), $p<0.05$). The bar labeled HSD represents the critical difference according to Tukey's HSD ($p<0.05$). Data points separated by a distance larger than this bar are significantly different.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by those of ordinary skill in the art, certain definitions are set forth to facilitate explanation of the presently-disclosed subject matter.

The presently-disclosed subject matter relates to combinations of topiramate and phentermine as well as methods for treating a subject who is experiencing or is at risk of experiencing an undesired consequence of stimulant use. The methods include administering an effective dose of a combination of topiramate and phentermine to a subject. Stimulant use, in some in embodiments, can include stimulant misuse, and the undesired consequences of stimulant use include those which are consistent with characterizations of use or misuse of a stimulant, including abuse of or dependence on the stimulant. In some embodiments, the undesired consequence of stimulant use is the craving for administration of a stimulant. In some embodiments, the stimulant is cocaine. As further described in the example provided below, combinations of topiramate and phentermine described herein have been found to attenuate the behavioral (i.e., reinforcing and subjective) effects of cocaine of subjects with cocaine use disorder. In this regard, methods of treating cocaine use disorder, which includes administering an effective dose of a combination of topiramate and phentermine to a subject with cocaine use disorder, are thus also provided herein.

Each respective method described herein may first include identifying a subject for treatment. Determination of a subject for whom treatment with a combination of topiramate and phentermine is indicated can be done by a healthcare professional who is trained to identify an individual experiencing an undesired consequence of stimulant use. Additionally or alternatively, subjects can self-assess their need for an intervention to address such consequences.

In some embodiments, the subject for whom treatment is provided may not have used the particular stimulant prior to the instance of stimulant use with which the undesired consequence is associated, i.e., the individual may not have a history of having been prescribed, been administered, or self-administered the stimulant(s) on a daily or regular basis. Such subject can include, for example, an individual, who is prescribed a stimulant by a medical provider and is using such stimulant for the first time and/or according to a prescribed treatment regimen as well as an individual who has recently began self-administering stimulant(s) for any reason. In other embodiments, the subject may be stimulant-experienced, i.e., may have a history of use of stimulants. In further embodiments, the subject may be highly stimulant experienced, and may be diagnosed with stimulant use disorder. In some embodiments, the subject may be diagnosed with cocaine use disorder.

As used herein, an "effective dose" or "effective amount" refers to a dose or an amount of a combination of topiramate and phentermine that is effective in treating the disorders, symptoms, or undesired consequence associated with use of a stimulant. In some embodiments, the effective dose is a dose which is effective to alleviate the undesired consequence(s) associated with the use of a particular stimulant. In various embodiments, the effective dose of a combination of topiramate and phentermine may be as follows: phentermine is administered in a dose of about 15 mg/day, or a dose of more than about 15 mg/day, or in a dose of about 15 mg/day to about 30 mg/day, or in a dose of about 30 mg/day; and topiramate is administered in a dose of about 50 mg/day, or in a dose of more than about 50 mg/day, or in a dose of about 50 mg/day to about 100 mg/day, or in a dose of about 100 mg/day.

In some embodiments of the methods disclosed herein, the combination of topiramate and phentermine is administered as a composition that includes both the topiramate and the phentermine. In other embodiments, the combination of topiramate and phentermine may be administered by administering a first composition which includes the topiramate and administering a second composition which includes the phentermine.

It is also recognized that one skilled in the art may affect the subject's experience of an undesired consequence of stimulant use by treating a subject presently afflicted with such a consequence or by prophylactically treating a subject who is using a stimulant, and has not yet experienced an undesired consequence, with an effective dose of a combination of topiramate and phentermine. Such a subject for whom prophylactic treatment may be indicated, may be said to be at risk of experiencing an undesired consequence of stimulant use including stimulant misuse, such as abuse or dependence. Since a subject continuing to use a stimulant is at risk for, and may experience, an undesired consequence during such continued use, prophylactic treatment can be indicated for any such subject who is continuing with stimulant use, including stimulant misuse.

Thus, with respect to the present use, the terms "treatment" and "treating" are intended to encompass any process wherein there may be a slowing, interrupting, arresting, controlling, or stopping of the undesired consequence of stimulant use. Thus, while the term includes prophylactic treatment for undesired consequences of stimulant use, it does not necessarily indicate a total prophylaxis of or complete elimination of the undesired consequence.

Without wishing to be bound by any particular theory, it is believed that topiramate, as a gamma aminobutyric acid (GABA) agonist and glutamate antagonist, and phentermine, as a monamine releaser, in combination may affect dysregulated neurotransmission between brain GABA, glutamate, and monoamine systems in a manner which results in the attenuation of the reinforcing effects of cocaine. In this regard, cocaine administration is known to increase synaptic dopamine (DA) levels. GABA systems inhibit DA systems and topiramate antagonizes glutamate transmission via AMPA/kainite receptors. Glutamate activity in the nucleus accumbens affects the action of GABA neurons, which in turn regulate DA activity in the mesocorticolimbic pathway. Topiramate may thus serve to affect brain GABA and glutamate system in manner which increases GABA activity and cause downstream decreases in DA action. Phentermine is a norepinephrine releaser, which affects central monoamine systems in a manner which has been found to attenuate the reinforcing effects of cocaine. As will be appreciated by those skilled in the art, the combinations of topiramate and phentermine and methods of treatment described herein are thus not necessarily limited to applications involving cocaine use, but rather may also be used in treating subjects who are experiencing or are at risk of experiencing an unintended consequence derived from the use of other stimulants which dysregulate neurotransmission between brain, GABA, glutamate, and monoamine systems.

Accordingly, in some embodiments, "stimulant" can refer to cocaine, while, in other embodiments, "stimulant" can refer to other prescription or non-prescription substances that raise levels of physiological and/or nervous system activity in the body of a subject, which has been found to result in an undesired consequence in subjects who use the substance.

Unless defined otherwise, all technical and scientific terms used herein have the same meaning as is commonly understood by one of skill in the art to which the invention(s) belong. All patents, patent applications, published applications and publications, GenBank sequences, databases, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

Although any methods, devices, and materials similar or equivalent to those described herein can be used in the practice or testing of the presently-disclosed subject matter, representative methods, devices, and materials are described herein.

The present application can "comprise" (open ended) or "consist essentially of" the components of the present invention as well as other ingredients or elements described herein. As used herein, "comprising" is open ended and means the elements recited, or their equivalent in structure or function, plus any other element or elements which are not recited. The terms "having" and "including" are also to be construed as open ended unless the context suggests otherwise.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, in some embodiments ±0.1%, in some embodiments ±0.01%, and in some embodiments ±0.001% from the specified amount, as such variations are appropriate to perform the disclosed methods.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, "optional" or "optionally" means that the subsequently described event or circumstance does or does not occur and that the description includes instances where said event or circumstance occurs and instances where it does not. For example, an optionally variant portion means that the portion is variant or non-variant.

The presently-disclosed subject matter is further illustrated by the following specific but non-limiting example. The following example may include compilations of data that are representative of data gathered at various times during the course of development and experimentation related to the present invention.

EXAMPLE

This example describes a mixed-model, placebo-controlled, inpatient study in which combinations of topiramate and phentermine were administered to subjects to assess the efficacy of topiramate-phentermine combinations as a pharmacotheraputic for treating stimulant use disorder and to identify topiramate-phentermine dose combinations which effectively attenuate the behavioral effects of a stimulant. In the study, respective subject groups were maintained on different topiramate dosages while concurrently being maintained on various phentermine dosages to assess the efficacy of various topiramate-phentermine combinations in treating subjects with cocaine use disorder. There is growing body of evidence which suggests that obesity and cocaine use disorder share common neurobiological substrates even though they are distinct clinical entities. Previous research has demonstrated that combinations of topiramate and phentermine are effective in treating obesity (i.e., promoting weight loss). The instant inventor has demonstrated that combinations of topiramate and phentermine can also be utilized as a pharmacotheraputic to robustly attenuate the behavioral effects of cocaine.

METHODS

Participants

Thirty-one (31) participants provided sober, written informed consent to participate and completed this mixed-model, placebo-controlled, inpatient study. In order to be eligible for the study, participants had to be healthy and without contraindications to cocaine, topiramate, or phentermine. Participants had to report recent use of cocaine, meet diagnostic criteria for a cocaine use disorder (i.e., abuse or dependence) according to a computerized Structured Clinical Interview for DSM-IV (SCID) that was reviewed by a psychiatrist or psychologist and provide a benzoylecgonine positive urine sample during screening to verify current cocaine use status. Screening procedures for all participants included a medical history questionnaire, laboratory chemistries (e.g., blood chemistry screen, complete blood count and urinalysis), electrocardiogram and a brief psychiatric examination. Participants were excluded from participation if a study physician deemed the screening results to be abnormal (e.g., electrocardiogram was outside normal limits). Participants with histories of serious physical disease, current physical disease or current or past histories of serious psychiatric disorder, including current or past histories of other substance abuse or dependence, that in the opinion of a study physician would have interfered with study participation (e.g., physiologic dependence on opioids, alcohol or benzodiazepines; schizophrenia; major depression; bipolar disorder) were also excluded. Decisions to exclude participants on these grounds were based on review of screening materials and/or history and physical examination conducted by a study physician. Female participants had to be using an effective form of birth control (e.g., birth control pills, IUD, condoms or abstinence) in order to participate.

General Procedures

Participants were enrolled as inpatients at the University of Kentucky Center for Clinical and Translational Science (CCTS) Clinical Services Core (CSC) for up to 33 days and completed a drug-free practice, a medical-safety session, and nine (9) experimental sessions. During inpatient admission, participants received standard caffeine-free hospital meals. Urine samples were collected daily and expired breath samples were collected prior to each session to confirm drug and alcohol abstinence, respectively. Pregnancy tests were conducted daily on urine samples from the female participants. All pregnancy tests were negative throughout their participation. When not in session, participants could smoke cigarettes periodically as long as CSC staff was available to escort them to the designated smoking area.

Practice Session

Participants completed a single practice session to familiarize them with the study procedures.

Medical Safety Session

Participants completed one, single-blind medical safety session to ensure they could tolerate intranasal cocaine. Intranasal cocaine doses (i.e., 0 [placebo], 10, 20, 40 and 80 mg) were administered in ascending order. Placebo (i.e., 0 mg) was administered at 0900 hours. The subjective-effect questionnaires and cardiovascular measures described below were completed 30 minutes before placebo administration (i.e., 0830 hours), immediately following and at 15-minute intervals for 45 minutes. Subsequent cocaine administrations were separated by 45 minutes.

Topiramate and Phentermine Maintenance

All drugs were administered in a double-blind fashion. Only study investigators and the Investigational Drug Service staff had access to dose orders in order to maintain the blind. These individuals did not interact with participants during experimental sessions, nor did they collect experimental data.

Drug maintenance began on the day immediately following the Medical Safety Session and continued throughout the protocol. Topiramate (0, 50, 100 mg/day) and phentermine (0, 15, 30 mg/day) were prepared by over-encapsulating commercially available doses in a size 0 capsule. All capsules were then filled with cornstarch. Placebo capsules were identical but contained only cornstarch.

The maintenance period for each condition was at least seven (7) days. Participants randomized to 50 or 100 mg/day topiramate initially received 12.5 and 25 mg immediate release topiramate, respectively, twice daily (0700 and 1900 hours) for three (3) days. Participants then received their target dose (i.e., 25 and 50 mg BID, respectively) for four (4) days prior to completing the first block of experimental sessions. This dosing regimen allowed participants to acclimate to a lower topiramate dose before receiving their target dose and was the rationale for topiramate being a between-subject variable. Participants randomized to placebo were also maintained for seven (7) days to maintain the study blind, but their capsules contained only cornstarch.

Phentermine (0, 15, 30 mg) was administered once daily at 0700 hours. Within each topiramate cohort, the phentermine doses were tested in ascending order such that the lower dose (15 mg/day) was tested prior to the higher dose (30 mg/day). This dosing sequence was violated twice due to oversight (i.e., one subject in the 0 mg/day topiramate group and the other in the 50 mg/day topiramate group). Both of these participants were initially maintained on 30 mg/day phentermine. Visual inspection of the behavioral and cardiovascular data suggests these individuals responded similarly to the other participants in their respective groups.

After at least seven (7) days of maintenance on the first topiramate-phentermine condition, participants completed a block of three experimental sessions described below. Maintenance on the assigned condition continued during each block of experimental sessions. Upon completion of the first block of experimental sessions, participants continued maintenance on the assigned topiramate condition, while the phentermine dose was changed to the next condition. Maintenance on the second topiramate-phentermine condition also lasted at least seven (7) days before the next block of experimental sessions was completed. Upon completion of the second block of experimental sessions, participants continued maintenance on the assigned topiramate condition, while the phentermine dose was changed to the final condition. Maintenance on the final topiramate-phentermine condition also lasted at least seven (7) days before the third block of three experimental sessions was completed. Participants were discharged from the study the day after completing the third block of experimental sessions.

Experimental Sessions

Participants received the appropriate maintenance doses at 0700 hours on the morning of all experimental sessions. Participants were allowed to smoke a cigarette prior to experimental sessions that started at 0900 hours and were not allowed to smoke again until the session ended approximately 7.5 hours later. Sessions consisted of a Sampling Phase and a Self-Administration Phase. These phases were separated by approximately three-hours during which time lunch was available.

Sampling Phase. Participants completed a sampling phase in each experimental session to acquaint them with the effects of the cocaine dose available during that session. Baseline subjective and physiological measures were completed at approximately 0900 hours. At approximately 0930 hours, the intranasal cocaine dose (0, 40 or 80 mg) available during that session was administered. Cocaine sampling doses (0, 40, 80 mg) were prepared by combining the appropriate amount of cocaine HCl (Medisca Inc., Plattsburgh, N.Y., NDC:38779-0723-03) with cornstarch to equal a total of 120 mg powder. During all cocaine administrations, a nurse presented the subject with the powder, a mirror and a standard razor blade. The participant was instructed to divide the powder into two even "lines" and insufflate one line of powder through each nostril using a 65-mm plastic straw within 2 min. Doses were not administered if heart rate was ≥100 bpm, systolic blood pressure was ≥150 mmHg or diastolic blood pressure was ≥100 mmHg or if clinically significant and/or prolonged ECG abnormalities were detected. These dosing thresholds (i.e., heart rate, systolic, and diastolic) were lowered to heart rate ≥90 bpm, systolic blood pressure ≥140 mmHg, and diastolic blood pressure ≥90 mmHg at the behest of the Food and Drug Administration (FDA) in the final year of the study. Cocaine dosing order was randomized for each subject. Immediately after dosing and at 15-minute intervals for the next hour, subjective, performance and physiological measures were completed. The sampling phase ended at approximately 1030 hours.

Self-Administration Phase. The self-administration phase began at approximately 1330 hours. During this phase, participants completed 10 trials in which they were required to choose between ⅒th of the cocaine dose insufflated during the sampling session or USD $0.25 on a progressive-ratio task (i.e., the sum of cocaine and money choices in each session was always 10).

The reinforcing effects of cocaine during maintenance on the topiramate-phentermine combinations were assessed using a progressive-ratio task. Participants were able to earn drug or money by responding on a computer mouse. Cocaine and money were available on concurrent, independent progressive-ratio schedules as described previously (Stoops et al., 2012). The initial ratio to obtain a reinforcer was 400 clicks. The response requirement for each subsequent choice of that specific reinforcer increased by 100 (i.e., 500, 600, 700, 800, 900, 1000, 1100, 1200, 1300 responses if a subject responded exclusively for cocaine or money). The dependent measure for this task was number of drug choices, out of a maximum of 10 (i.e., 100% of the sampling dose). Each potential cocaine amount participants could earn (e.g., 4, 8, 12, 16, 20, 24, 28, 32, 36 and 40 mg for the 40 mg dose) was admixed with cornstarch to equal a total of 120 mg powder. Following completion of the task, the research assistant communicated the appropriate blinded dose code to the nursing staff (e.g., 4 mg in the 40 mg dose condition was labeled Dose 1), who then presented the dose to the subject for self-administration. Participants then insufflated the chosen dose, at approximately 1415 hours, and completed subjective and physiological measures at 15-minute intervals for 60 minutes. Sessions ended at approximately 1515 hours.

Subjective Effects Questionnaire

Subjective measures included a locally developed Drug-Effect Questionnaire (Rush et al., 2003) and the Adjective Rating Scale (Oliveto et al., 1992). These measures have previously been shown to be sensitive to the effects of stimulants (Rush et al., 2009).

Cardiovascular Measures

Heart rate, blood pressure, and heart rhythmicity (via ECG) were recorded using a Dinamap digital monitor (Critikon, Pro 1000, Tampa, Fla.). Telemetry-certified nurses interpreted the results of the ECG with instructions to contact a study physician regarding abnormalities.

Discontinuation of Topiramate

Upon discharge, participants were tapered off topiramate. Each participant received fourteen (14) envelopes (i.e., doses for 0700 and 1900 hours for seven days). The first eight envelopes contained half of their target dose (i.e., 12.5 or 25 mg BID). The remaining six envelopes contained placebo. Participants maintained on placebo were given envelopes that contained placebo capsules only.

Subject Payment

Participants were paid $40 for each day they resided on the CSC and received a $40 completion allowance for these days if they completed the entire experiment. The amount earned by the subject was disbursed to them upon completion of the study and during follow up visits. Payments were disbursed once per week following discharge in amounts up to $500 dollars until the subject was paid in full. When participants returned on a weekly basis to receive their payments, we surveyed them regarding their drug use since being discharged from the study. Participants could also earn up to a total of $22.50 on the progressive-ratio task across all sessions, depending on their choices between drug and money. A maximum of $2842.50 could be earned for participating in the study.

Data Analysis

Data was analyzed using analysis of variance (ANOVA; Statview, Cary, N.C.) as described below. Planned comparisons were then conducted as appropriate using Tukey's Honestly Significantly Different (HSD). Effects with $p \leq 0.05$ were considered significant for all statistical analyses.

Demographics data were analyzed using a one-way ANOVA with Topiramate Group (0, 50, 100 mg/day) as a between-subject factor. Planned comparisons (i.e., Tukey's HSD) were then conducted to make pairwise comparisons between each of the three groups. Categorical data (i.e., sex and race) were analyzed using Chi Square.

Subjective and cardiovascular data from the Medical Safety Session were analyzed as peak effect (i.e., the maximum score observed following an administration of a cocaine dose (0, 10, 20, 40, 80 mg) using mixed-model ANOVA with Topiramate Group (0, 50, 100 mg/day; between-subject factor) and Cocaine (0, 10, 20 40, 80 mg, within-subject factor) as the variables. Planned comparisons (i.e., Tukey's HSD) were then conducted first to compare active cocaine doses to placebo (0 mg) within each Topiramate Group. Corresponding doses were then compared when a cocaine dose produced a significant effect in any of the Topiramate groups.

Progressive-ratio data from the Experimental Sessions were analyzed as number of drug choices using a three-factor mixed-model ANOVA with Topiramate Group (0, 50, 100 mg/day; between-subject factor), Phentermine (0, 15, 30 mg/day, within-subject factor) and Cocaine (0, 40, 80 mg, within-subject factor) as the variables. Planned comparisons (i.e., Tukey's HSD) were then conducted first to compare active cocaine doses (40 and 80 mg) and placebo (0 mg) during Topiramate (0 mg/day)+Phentermine (0 mg/day) maintenance. Subsequent planned comparisons determined differences between the cocaine doses (0, 40, 80 mg) under each of the maintenance conditions relative to 0 mg cocaine during Topiramate (0 mg/day)+Phentermine (0 mg/day) maintenance. Finally, the effects of the cocaine (40 or 80 mg) during maintenance on a topiramate-phentermine combination were compared if the cocaine dose produced a significant effect during topiramate (0 mg/day)+phentermine (0 mg/day) maintenance. Subjective and cardiovascular measures were analyzed as peak effect (i.e., the maximum score observed in the 60 min following administration of the cocaine sampling dose) in the same fashion as data from the progressive-ratio task.

Although there are not specific guidelines for choosing a primary outcome for efficacy trials for cocaine use disorder, percent patients abstinent during the final weeks of the trial is endorsed by the FDA. To more closely approximate this FDA-endorsed outcome measure, self-administration data as percent of participants who abstained entirely from cocaine self-administration was also analyzed. A participant was considered to have abstained when he/she did not self-administer any cocaine during the experimental sessions in which active doses were tested. Only four conditions were included in this analysis: topiramate (0 mg/day)+phentermine (0 mg/day), topiramate (0 mg/day)+phentermine (30 mg/day), topiramate (100 mg/day)+phentermine (0 mg/day), and topiramate (100 mg/day)+phentermine (30 mg/day). Odds ratios were calculated for appropriate pairwise comparisons.

RESULTS

Demographics

Table 1 shows the demographics and substance use of the participants for each of the topiramate groups. Data presented in Table 1 are Means (Standard Deviation). In no instance was there a significant difference between the topiramate groups (Tukey's HSD, $p > 0.05$).

TABLE 1

|  | TOP (0 mg) (N = 11) | TOP (50 mg) (N = 9) | TOP (100 mg) (N = 11) |
|---|---|---|---|
| Demographics |  |  |  |
| Age | 44.8(5.42) | 42.2(11.9) | 44.5(2.5) |
| Female | 3 | 1 | 3 |
| Race |  |  |  |
| Caucasian | 2 | 3 | 3 |
| African American | 9 | 6 | 8 |
| Education (Years) | 12.6(1.1) | 12.3(0.9) | 12(1.5) |
| Alcohol and Cigarette Use |  |  |  |
| DAST | 8.0(54.9) | 6.6(3.5) | 11(5.2) |
| MAST | 8.2(7.7) | 3.1(4.1) | 11(10.5) |

TABLE 1-continued

|  | TOP (0 mg) (N = 11) | TOP (50 mg) (N = 9) | TOP (100 mg) (N = 11) |
|---|---|---|---|
| AUD1T | 7.4(7.6) | 3.8(2.6) | 7.5(6.3) |
| Drinks/Week | 10.8(13.5) | 6.2(7.8) | 15.5(17.4) |
| Tabacco Cigarettes/Day | 9.8(7.2) | 8.0(5.6) | 9.3(7.0) |
| Cocaine Use | | | |
| Years Used | 23.3(6.7) | 16.3(10.3) | 21.6(4.7) |
| Days Used past week | 3.0(1.3) | 3.3(1.5) | 2.9(1.8) |
| Days Used Past Month | 13.5(6.7) | 12.3(6.5) | 12.3(7.6) |
| Money Spent Past Week ($) | 84.1(78.4) | 114.4(139.3) | 116.4(127.8) |
| Money Spent Past Month ($) | 367.7(219.0) | 430.0(457.9) | 470.9(701.0) |
| Past Month Drug Use | | | |
| Days Used Opioids | 0.1(54.9) | 0.8(2.3) | 0.3(0.7) |
| Days Used Cannabis | 13.2(54.9) | 8.1(10.6) | 10.0(12.6) |

Note:
All values presented as mean (standard deviation) or counts/percentages.
TOP = Topiramate;
MAST = Michigan Alcohol Screening Test;
DAST = Drug Abuse Screening Test.

Medical Safety Session

Note that, although there are references to topiramate groups below, the effects of cocaine on subjective effects questionnaires and cardiovascular measures were assessed before topiramate maintenance began.

Subjective Effects Questionnaires. Table 2 shows the mean peak effect for cocaine (0, 10, 20, 40, 80 mg) for each of the topiramate groups (0, 50, 100 mg/day) during the medical safety session. The rightmost column shows the critical difference according to Tukey's Honestly Significant Difference (HSD) ($p<0.05$). Data points differing by this value or more are significantly different. Bold and underlined values are significantly different from the placebo dose for the group.

TABLE 2

| | Topiramate (0 mg/day) Cocaine (mg) | | | | Topiramate (50 mg/day) Cocaine (mg) | | | | Topiramate (100 mg/day) Cocaine (mg) | | | | Tukey's HSD |
|---|---|---|---|---|---|---|---|---|---|---|---|---|---|
| | 0 | 10 | 20 | 40 | 80 | 0 | 10 | 20 | 40 | 80 | 0 | 10 | 20 | 40 | 80 | |

| Adjective Rating Scales | | | | | | | | | | | | | | | | |
|---|---|---|---|---|---|---|---|---|---|---|---|---|---|---|---|---|
| Sedative | 2.2 | 2.0 | 4.6 | 3.2 | 4.1 | 3.2 | 3.9 | 2.8 | 2.1 | 2.4 | 2.8 | 3.1 | 3.7 | 5.1 | 7.8 | 5.0 |
| Stimulant | 4.6 | 6.1 | 8.4 | 0.0 | 6.5 | 8.7 | 8.7 | 8.6 | 10.1 | 13.2 | 10.8 | 10.6 | 11.1 | 11.8 | 15.7 | 4.1 |
| Drug-Effect Questionnaire | | | | | | | | | | | | | | | | |
| Active-Alert-Energetic | 10.6 | 17.0 | 23.5 | 26.0 | 25.6 | 5.8 | 11.2 | 12.8 | 24.7 | 31.4 | 6.4 | 6.4 | 11.0 | 13.8 | 24.5 | 16.3 |
| Any Effect | 11.8 | 21.5 | 28.6 | 33.3 | 38.1 | 3.2 | 7.0 | 9.9 | 19.3 | 29.6 | 8.3 | 10.7 | 11.7 | 22.1 | 38.5 | 2.3 |
| Bad Effects | 2.8 | 4.4 | 4.5 | 9.0 | 6.2 | 0.4 | 1.2 | 0.3 | 7.2 | 10.4 | 0.2 | 0.2 | 2.2 | 3.0 | 12.2 | 17.0 |
| Euphoria | 8.6 | 10.1 | 11.5 | 10.6 | 10.5 | 4.3 | 3.4 | 12.4 | 8.2 | 14.7 | 1.9 | 5.8 | 5.7 | 8.7 | 16.2 | 18.7 |
| Good Effects | 11.4 | 21.5 | 26.3 | 33.9 | 33.3 | 5.9 | 6.4 | 11.2 | 17.0 | 24.0 | 8.8 | 14.5 | 10.2 | 24.0 | 27.9 | 21.0 |
| High | 10.4 | 17.3 | 20.0 | 29.5 | 27.7 | 4.7 | 6.1 | 13.1 | 29.0 | 31.8 | 7.2 | 7.4 | 12.8 | 23.6 | 42.0 | 24.0 |
| Irregular Heart Beat | 4.6 | 7.0 | 8.8 | 7.4 | 14.4 | 0.0 | 8.6 | 0.6 | 8.0 | 0.8 | 0.1 | 2.8 | 3.2 | 9.0 | 24.1 | 18.8 |
| Like Drug | 9.7 | 25.2 | 27.8 | 36.1 | 34.6 | 9.1 | 9.2 | 14.6 | 16.7 | 28.4 | 11.5 | 10.1 | 14.9 | 20.8 | 32.4 | 22.0 |
| Nausea-Queasy-Sick | 2.5 | 3.3 | 2.9 | 3.2 | 8.8 | 3.9 | 1.2 | 2.2 | 9.8 | 1.2 | 0.1 | 6.8 | 10.6 | 16.2 | 26.5 | 26.8 |
| Nervous-Anxious | 5.8 | 5.1 | 8.5 | 10.1 | 12.1 | 0.0 | 0.3 | 0.0 | 1.8 | 2.2 | 1.5 | 0.2 | 6.8 | 8.1 | 22.9 | 19.2 |
| Performance Impaired | 3.8 | 4.9 | 10.4 | 10.7 | 10.5 | 0.0 | 0.9 | 2.4 | 1.9 | 1.9 | 0.2 | 0.2 | 5.5 | 4.1 | 12.9 | 13.7 |
| Performance Improved | 5.4 | 10.7 | 12.0 | 10.7 | 11.5 | 0.7 | 3.3 | 5.4 | 10.6 | 11.2 | 0.1 | 2.1 | 4.0 | 5.0 | 9.5 | 16.0 |
| Restless | 7.6 | 7.9 | 8.9 | 10.4 | 10.1 | 0.1 | 1.2 | 0.7 | 2.9 | 7.6 | 2.6 | 0.7 | 0.2 | 9.1 | 11.1 | 16.4 |
| Rush | 9.3 | 15.5 | 19.4 | 28.1 | 27.3 | 1.4 | 5.9 | 14.8 | 30.0 | 28.4 | 4.5 | 6.9 | 12.4 | 20.1 | 36.1 | 24.4 |
| Shaky-Jittery | 4.9 | 3.9 | 8.8 | 0.7 | 13.8 | 0.0 | 1.4 | 1.1 | 2.8 | 4.8 | 0.3 | 0.3 | 3.1 | 8.7 | 22.1 | 19.9 |
| Sluggish-Fatigued-Lazy | 4.1 | 8.1 | 6.8 | 9.0 | 5.7 | 0.0 | 5.4 | 0.8 | 0.1 | 0.0 | 0.1 | 0.5 | 1.1 | 9.1 | 22.0 | 18.4 |
| Stimulated | 9.8 | 13.8 | 18.7 | 21.1 | 21.1 | 6.8 | 11.9 | 15.8 | 22.3 | 31.8 | 5.2 | 7.7 | 10.5 | 16.5 | 31.1 | 20.1 |
| Talkative-Friendly | 8.9 | 17.8 | 18.6 | 16.7 | 17.9 | 1.0 | 4.7 | 10.2 | 18.8 | 14.3 | 2.5 | 7.8 | 11.2 | 13.2 | 16.1 | 13.0 |
| Willing to Pay For | 9.9 | 20.6 | 24.9 | 32.6 | 30.5 | 6.9 | 5.4 | 7.6 | 17.0 | 30.6 | 8.6 | 8.6 | 11.7 | 15.0 | 21.0 | 22.7 |
| Willing to Take Again | 14.6 | 26.3 | 32.9 | 40.6 | 38.4 | 15.4 | 12.0 | 10.2 | 17.4 | 30.3 | 19.0 | 12.8 | 11.8 | 18.4 | 33.8 | 29.4 |
| Vitals | | | | | | | | | | | | | | | | |
| Heart Rate | 72.8 | 70.9 | 77.9 | 74.8 | 85.8 | 87.9 | 67.4 | 66.6 | 70.8 | 78.0 | 65.1 | 66.7 | 64.6 | 67.8 | 77.6 | 10.8 |
| Systolic Pressure | 124.4 | 121.1 | 125.3 | 124.9 | 130.5 | 125.2 | 123.9 | 131.8 | 129.9 | 133.8 | 119.3 | 125.1 | 128.3 | 131.7 | 137.4 | 12.0 |
| Diastolic Pressure | 72.1 | 77.2 | 81.5 | 81.6 | 85.9 | 81.2 | 84.8 | 84.1 | 82.4 | 84.8 | 80.0 | 82.6 | 82.3 | 86.5 | 88.3 | 9.0 |

As shown in Table 2, at least one dose of cocaine significantly increased ratings on 13 items from Drug Effect Questionnaire in at least one of the topiramate groups (Tukey's HSD, p<0.05). There were only three instances of significant differences between the topiramate groups in terms of their responses to cocaine (i.e., ratings of Irregular Heartbeat, Nervous-Anxious, and Sluggish-Fatigued-Lazy; Tukey's HSD, p<0.05). In each instance, 80 mg cocaine produce significantly greater effects in the 100 mg/day topiramate group relative to the 50 mg/day topiramate group.

Table 2 also shows the subjective effects of cocaine during the medical safety session. Cocaine (40 or 80 mg) significantly increased scores on the Stimulant Subscale of the Adjective Rating Scale above placebo levels in each of the topiramate groups (Tukey's HSD, p<0.05). Cocaine (80 mg) produced significantly greater increases in the 50 and 100 mg/day topiramate groups relative to the 0 mg/day topiramate group (Tukey's HSD, p<0.05). Cocaine (80 mg) significantly increased scores on the Sedative Subscale above placebo levels in the 100 mg/day topiramate group (Tukey's HSD, p<0.05). This response was significantly different from responses to this cocaine dose in the 50 mg/day topiramate group. Cardiovascular Measures. Table 2 above also shows the cardiovascular effects of cocaine during the medical safety session. Cocaine (20, 40 or 80 mg) generally increased heart rate and blood pressure significantly increased heart rate or blood pressure significantly above placebo levels in at least one of the topiramate groups (Tukey's HSD, p<0.05). The effects of cocaine on heart rate and blood pressure were not significantly different across the topiramate groups.

Experimental Sessions

Figure 1B:
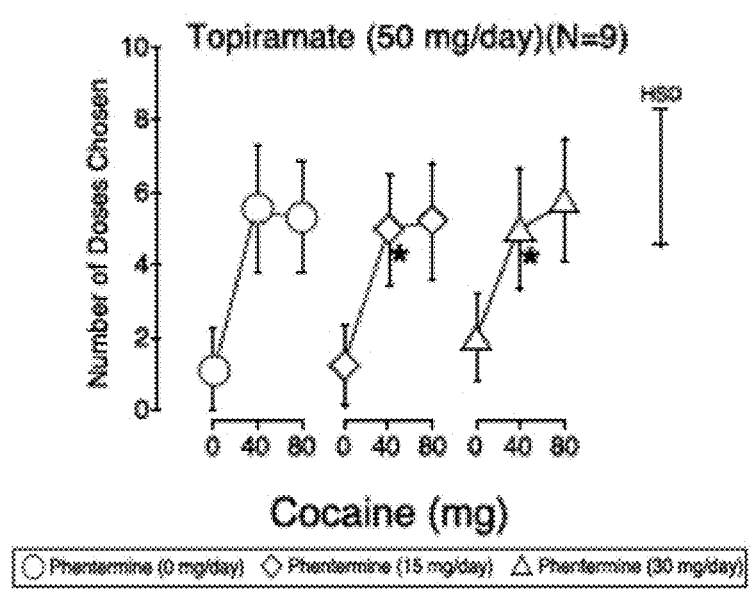
Figure 1C:
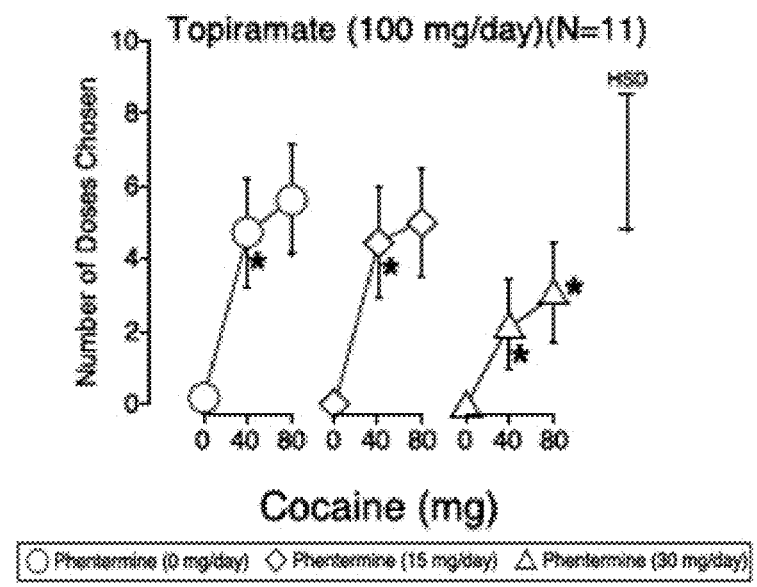

Cocaine Self-Administration. FIGS. 1A-C show the self-administration results of the different topiramate (0, 50, 100 mg) groups. Cocaine (40 and 80 mg) significantly increased the number of drug choices on the progressive-ratio procedure during maintenance on topiramate (0 mg/day)+phentermine (0 mg/day) relative to placebo (Tukey's HSD, p<0.05). Maintenance on topiramate (100 mg/day)+phentermine (0 mg/day) significantly reduced the number of cocaine (40 mg) choices relative to this cocaine dose during maintenance on topiramate (0 mg/day) +phentermine (0 mg/day) (FIGS. 1A and 1C) (Tukey's HSD, p<0.05). Maintenance on topiramate (50 mg/day)+phentermine (both 15 and 30 mg/day) significantly reduced the number of cocaine (40 mg) choices relative to this cocaine dose during maintenance on topiramate (0 mg/day)+phentermine (0 mg/day) (FIGS. 1A and 1B) (Tukey's HSD, p<0.05). Similar effects were observed during maintenance on topiramate (100 mg/day)+phentermine (both 15 and 30 mg/day) (FIG. 1C) (Tukey's HSD, p<0.05). Maintenance on topiramate (100 mg/day)+phentermine (30 mg/day) also significantly reduced the number of cocaine (80 mg) choices relative to this cocaine dose during maintenance on topiramate (0 mg/day)+phentermine (0 mg/day) (FIGS. 1A and 1C) (Tukey's HSD, p<0.05).

Figure 2:
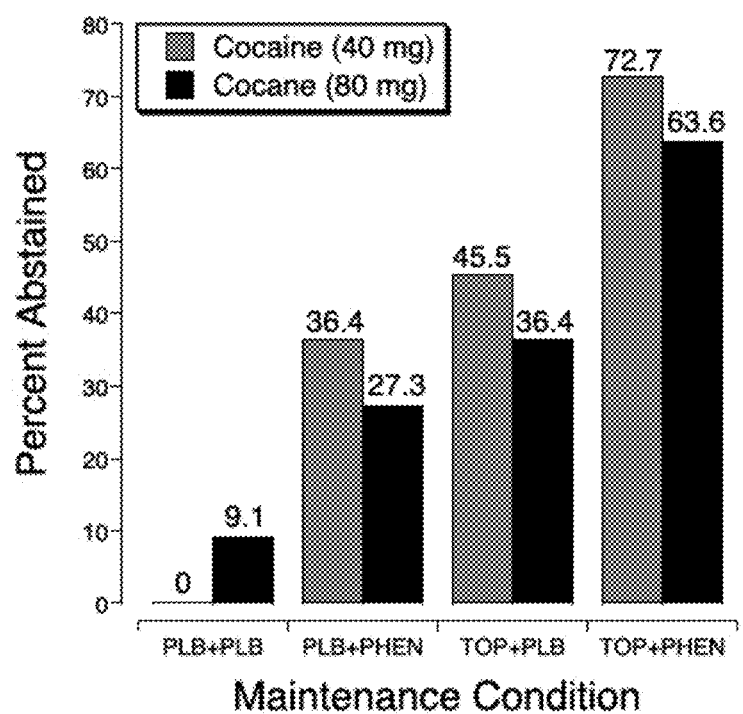
FIG. 2 is a graph showing the percent of participants who abstained from cocaine (40 and 80 mg) self-administration when maintained on topiramate (TOP) (TOP, 0 mg/day) plus phentermine (PHEN) (PHEN, 0 mg/day) (i.e., PLB+PLB); topiramate (TOP, 0 mg/day) plus phentermine (PHEN, 30 mg/day) (i.e., PLB+PHEN); topiramate (TOP, 100 mg/day) plus phentermine (PHEN, 0 mg/day) (i.e., TOP+PLB); and topiramate (TOP, 100 mg/day) plus phentermine (PHEN, 30 mg/day) (i.e., (TOP+PHEN).
Figure 3A:
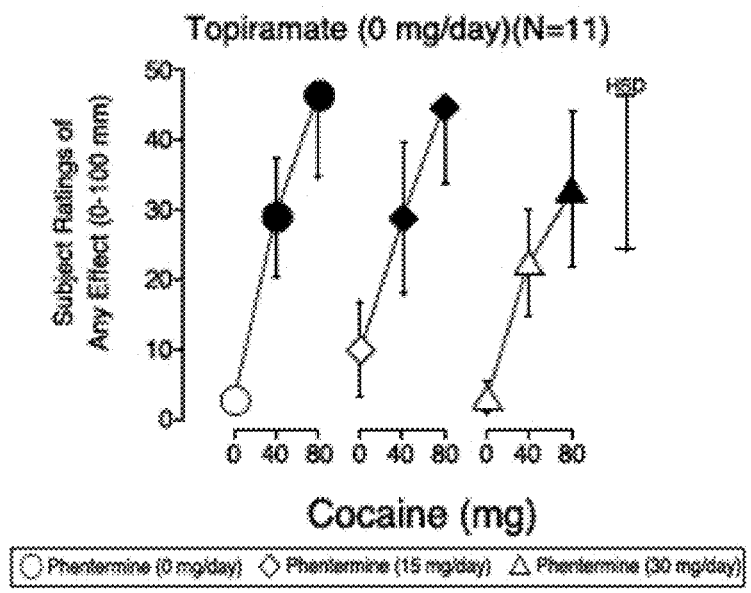
FIGS. 3A-F are graphs showing the mean (±SEM) peak subject ratings of Any Effect (A-C) and Good Effects (D-F) from the Drug-Effect Questionnaire. (A) (±SEM) peak subject ratings of Any Effect for cocaine (0, 40, 80mg) during maintenance on topiramate (0 mg/day) and phentermine (0, 15, 30 mg/day). (B) (±SEM) peak subject ratings of Any Effect for cocaine (0, 40, 80mg) during maintenance on topiramate (50 mg/day) and phentermine (0, 15, 30 mg/day). (C) (±SEM) peak subject ratings of Any Effect for cocaine (0, 40, 80 mg) during maintenance on topiramate (100 mg/day) and phentermine (0, 15, 30 mg/day). (D) (±SEM) peak subject ratings of Good Effects for cocaine (0, 40, 80 mg) during maintenance on topiramate (0 mg/day) and phentermine (0, 15, 30 mg/day). (E) (±SEM) peak subject ratings of Good Effects for cocaine (0, 40, 80 mg) during maintenance on topiramate (50 mg/day) and phentermine (0, 15, 30 mg/day). (F) (±SEM) peak subject ratings of Good Effects for cocaine (0, 40, 80 mg) during maintenance on topiramate (100 mg/day) and phentermine (0, 15, 30 mg/day). Filled symbols indicate a significant difference from 0 mg cocaine during maintenance on 0 mg topiramate and 0 mg phentermine (far left circle). An asterisk (*) indicates a significant difference from maintenance on topiramate (0 mg/day) and phentermine (0 mg/day) at a given dose of cocaine (Tukey's HSD, $p<0.05$). The bar labeled HSD represents the critical difference according to Tukey's HSD ($p<0.05$). Data points separated by a distance larger than this bar are significantly different.
Figure 3B:
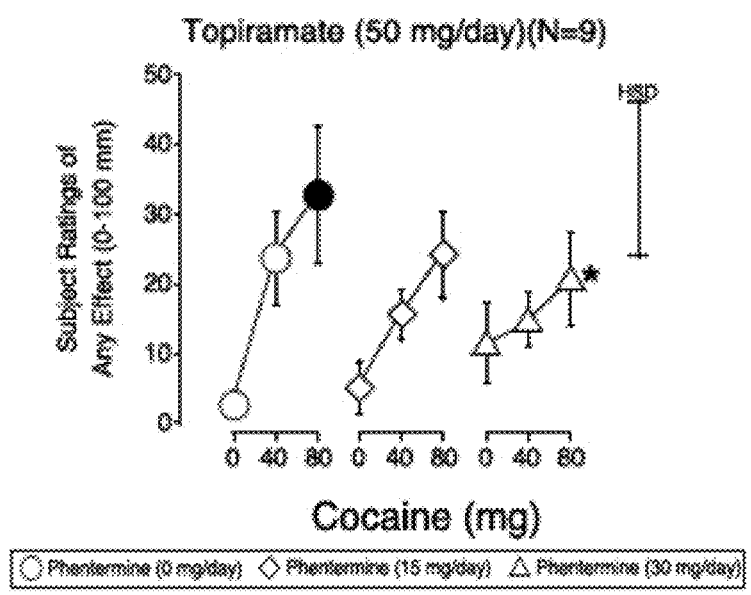
Figure 3C:
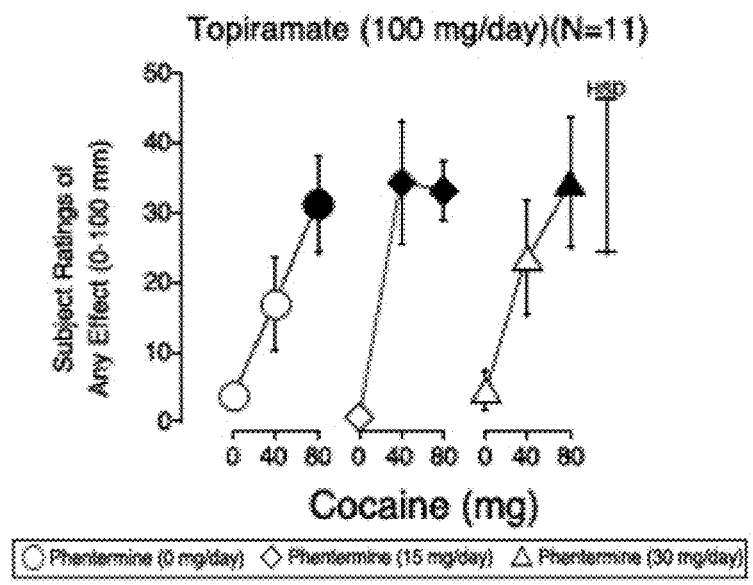
Figure 3D:
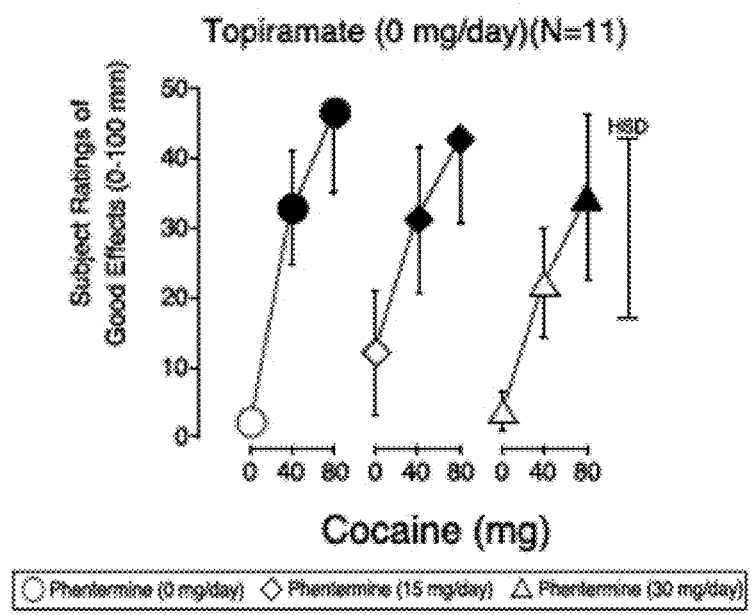
Figure 3E:
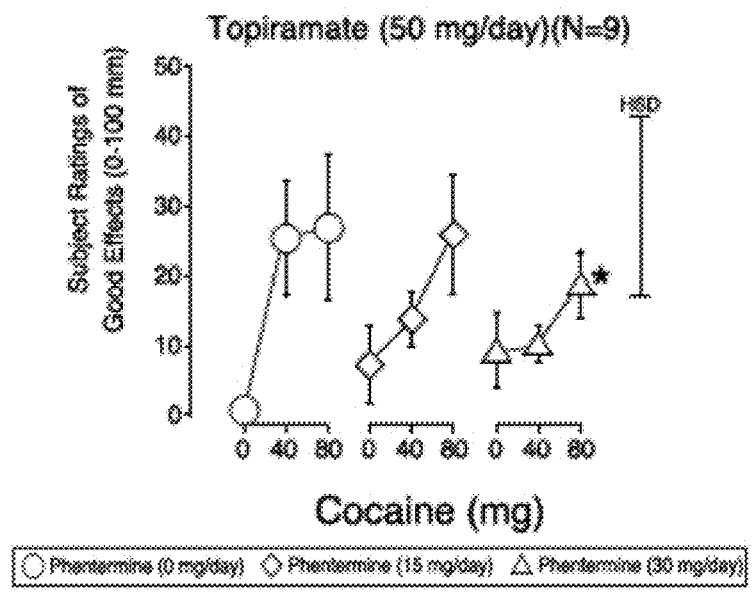
Figure 3F:
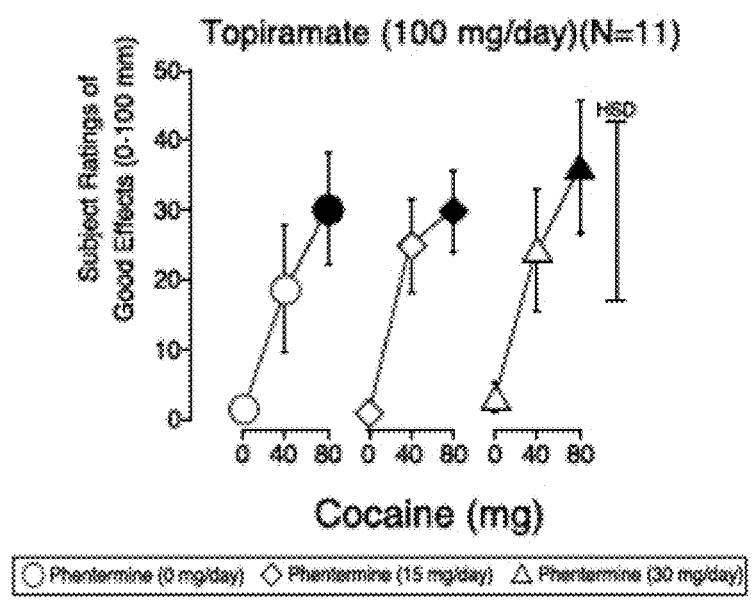
Figure 4A:
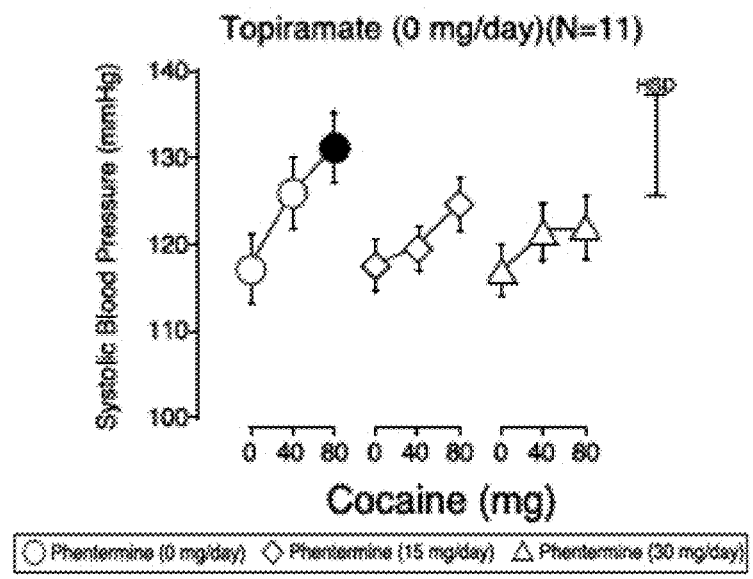
FIGS. 4A-F are graphs showing the effects of cocaine during each of the maintenance conditions for systolic (A-C) and diastolic (D-F) blood pressure. (A) Effects of cocaine (0, 40, 80 mg) on systolic blood pressure during maintenance on topiramate (0 mg/day) and phentermine (0, 15, 30 mg/day). (B) Effects of cocaine (0, 40, 80 mg) on systolic blood pressure during maintenance on topiramate (50 mg/day) and phentermine (0, 15, 30 mg/day). (C) Effects of cocaine (0, 40, 80 mg) on systolic blood pressure during maintenance on topiramate (100 mg/day) and phentermine (0, 15, 30 mg/day). (D) Effects of cocaine (0, 40, 80 mg) on diastolic blood pressure during maintenance on topiramate (0 mg/day) and phentermine (0, 15, 30 mg/day). (E) Effects of cocaine (0, 40, 80 mg) on diastolic blood pressure during maintenance on topiramate (50 mg/day) and phentermine (0, 15, 30 mg/day). (F) Effects of cocaine (0, 40, 80 mg) on diastolic blood pressure during maintenance on topiramate (100 mg/day) and phentermine (0, 15, 30 mg/day). Filled symbols indicate a significant difference from 0 mg cocaine during maintenance on 0 mg topiramate and 0 mg phentermine (far left circle). An asterisk (*) indicates a significant difference from maintenance on topiramate (0 mg/day) and phentermine (0 mg/day) at a given dose of cocaine (Tukey's HSD, $p<0.05$). The bar labeled HSD represents the critical difference according to Tukey's HSD ($p<0.05$). Data points separated by a distance larger than this bar are significantly different.
Figure 4B:
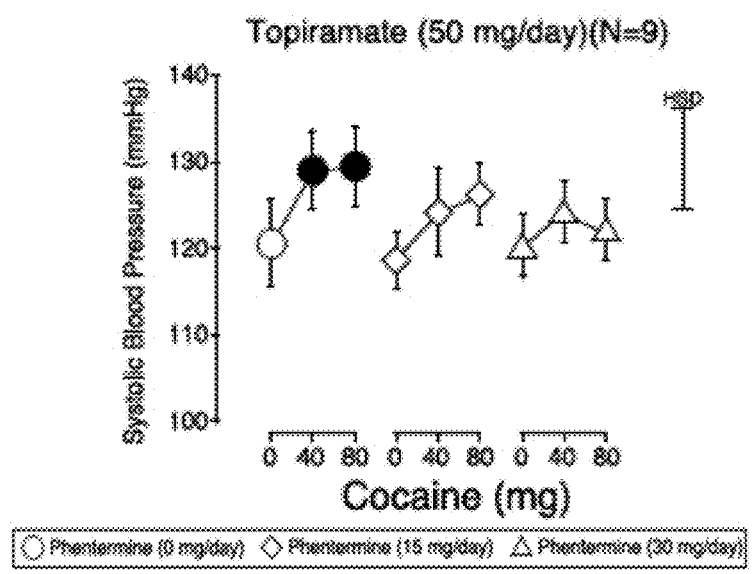
Figure 4C:
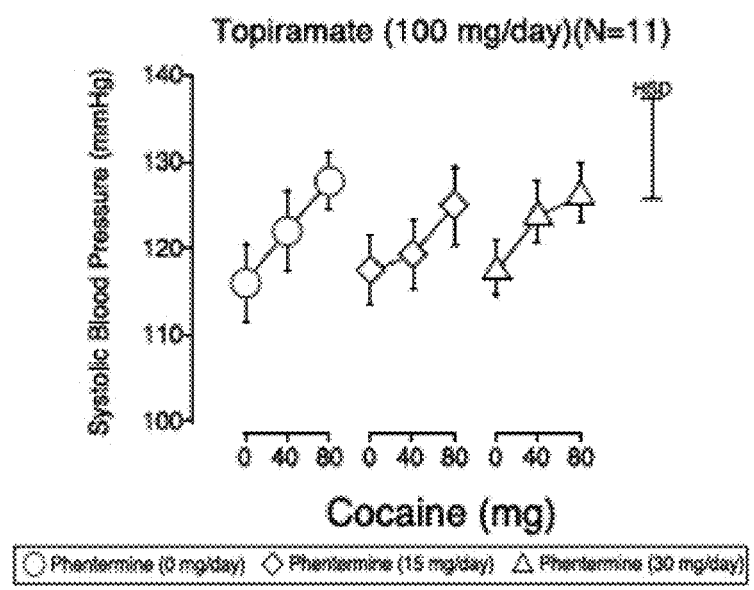
Figure 4D:
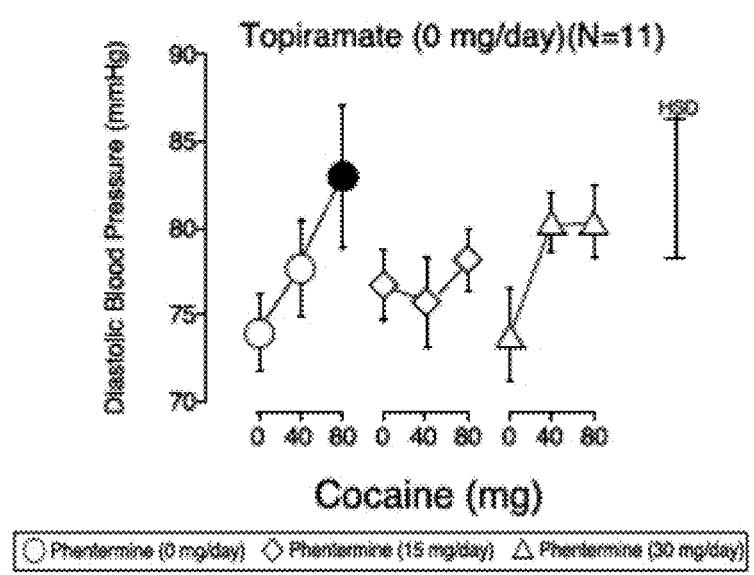
Figure 4E:
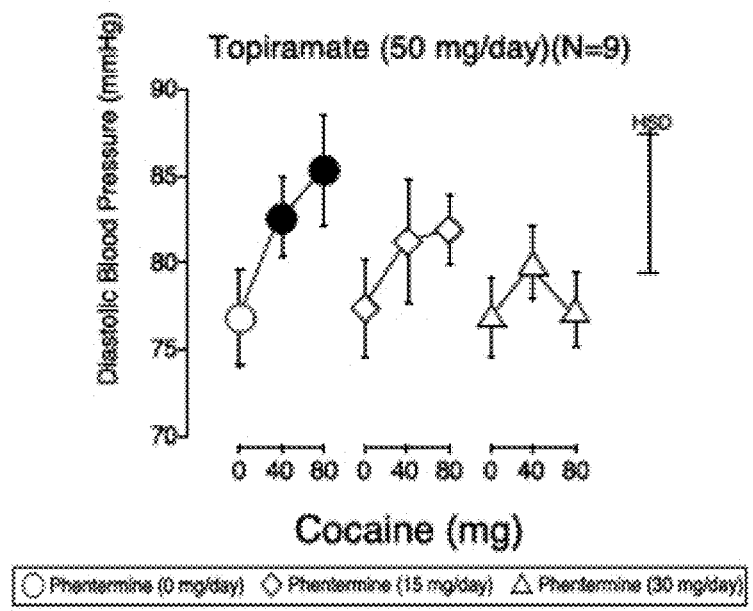
Figure 4F:
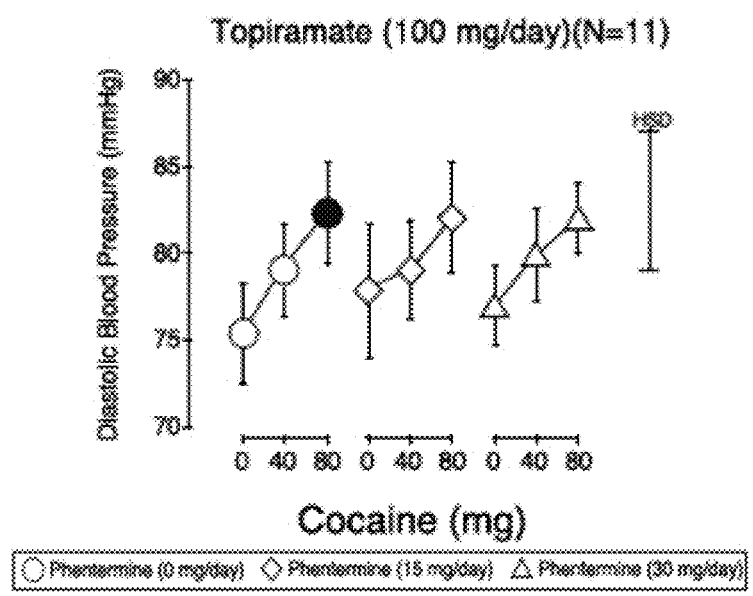

FIG. 2 shows the percent of participants who abstained during sessions when 40 or 80 mg cocaine was available. The topiramate (100 mg/day)+phentermine (30 mg/day) condition significantly increased the percent of participants who abstained relative to the topiramate (0 mg/day)+phentermine (0 mg/day) when 40 mg (OR=0.0179, 95% CI=0.0008-0.3946, p=0.0108) and 80 mg cocaine were available (OR=0.0571, 95% CI=0.0052-0.6266, p=0.0192). There were no other significant differences.

Subjective Effects Questionnaires. FIGS. 3A-F show the effects of cocaine during each of the maintenance conditions for ratings of Any Effect (FIGS. 3A-C) and Good Effects (FIGS. 3D-F) from the Drug Effect Questionnaire. Cocaine (40 and 80 mg) significantly increased these ratings during maintenance on topiramate (0 mg/day)+phentermine (0 mg/day) relative to cocaine (0 mg) during this maintenance condition (Tukey's HSD, p<0.05). Topiramate (50 mg/day)+Phentermine (30 mg/day) significantly decreased the effects of cocaine (80 mg) on both of these measures (Tukey's HSD, p<0.05). None of the other maintenance conditions significantly altered the effects of cocaine on these measures. Cocaine alone (40 and 80 mg) also significantly increased subject ratings of Willing to Pay For and Willing to Take Again during maintenance on topiramate (0 mg/day)+phentermine (0 mg/day) relative to cocaine (0 mg) during this maintenance condition (Tukey's HSD, p<0.05) (data not shown). Topiramate (50 mg/day)+phentermine (15 mg/day) significantly decreased the effects of cocaine (40 and 80 mg) on both of these measures (Tukey's HSD, p<0.05). None of the other maintenance conditions significantly altered these effects of cocaine on these measures. Cocaine (40 and 80 mg) significantly increased ratings of High and Like Drug on the Drug Effect Questionnaire during maintenance on topiramate (0 mg/day)+phentermine (0 mg/day) relative to cocaine (0 mg) during this maintenance condition (Tukey's HSD, p<0.05) (data not shown). Cocaine (80 mg) significantly increased ratings of Active-Alert-Energetic and Rush during maintenance on topiramate (0 mg/day)+phentermine (0 mg/day) relative to cocaine (0 mg) during this maintenance condition (Tukey's HSD, p<0.05) (data not shown). Similar results were observed on the Stimulant Subscale of the Adjective Rating Scale. Topiramate and phentermine, alone or combined, did not significantly alter these ratings Cocaine (40 or 80 mg) alone did not significantly increase ratings of Bad Effects, Euphoric, Irregular Heartbeat, Nausea-Queasy-Sick, Nervous-Anxious, Performance Impaired, Performance Improved, Restless, Shaky-Jittery, Sluggish-Fatigued-Lazy, Stimulated or Talkative-Friendly on the Drug Effect Questionnaire during maintenance on topiramate (0 mg/day)+phentermine (0 mg/day) relative to cocaine (0 mg) during this maintenance condition (Tukey's HSD, p>0.05) (data not shown). Similar results were observed on the Sedative Subscale of the Adjective Rating Scale.

Cardiovascular Measures. FIGS. 4A-F show the effects of cocaine during each of the maintenance conditions for systolic (FIGS. 4A-C) and diastolic (FIGS. 4D-F) blood pressure. Cocaine (80 mg) significantly increased systolic and diastolic blood pressure during maintenance on topiramate (0 mg/day)+phentermine (0 mg/day) relative to cocaine (0 mg) during this maintenance condition (Tukey's HSD, p<0.05). None of the other maintenance conditions significantly altered the pressor effect of cocaine. Cocaine (80 mg) significantly increased heart rate during maintenance on topiramate (50 or 100 mg/day)+phentermine (0 mg/day) relative to cocaine (0 mg) during maintenance on topiramate (0 mg/day)+phentermine (0 mg/day) (Tukey's HSD, p<0.05). No other significant effects were observed on heart rate.

DISCUSSION

The above-described experiment determined the behavioral (i.e., reinforcing and subjective) and cardiovascular (i.e., heart rate and blood pressure) effects of intranasal cocaine (0, 40, 80 mg) during maintenance on topiramate (0, 50, 100 mg/day) in separate cohorts of non-treatment seeking participants with cocaine use disorder concurrently maintained on phentermine (0, 15, 30 mg/day).

Cocaine, Topiramate, and Phentermine Alone

Cocaine alone functioned as a reinforcer (i.e., maintained self-administration) and produced prototypical subjective and cardiovascular effects. The constellation and magnitude of effects observed here were qualitatively and quantitatively similar to those observed previously with intranasal cocaine in our laboratory and others.

Topiramate alone (100 mg/day) significantly reduced cocaine (40 mg) self-administration in the present study, although this effect was moderate in magnitude (i.e., 47%). Topiramate maintenance did not alter the subjective or cardiovascular effects of cocaine to a statistically significant degree. Phentermine alone did not significantly alter the reinforcing, subjective, or cardiovascular effects of cocaine.

Phentermine alone did not significantly reduce cocaine self-administration in the present study.

Topiramate-Phentermine Combinations

Combining topiramate and phentermine significantly reduced cocaine self-administration in the present study. Combining topiramate (100 mg/day) and phentermine (30 mg/day) decreased cocaine (40 and 80 mg) self-administration by 76% and 61%, respectively. Together, these are the largest reductions in drug taking observed in a human laboratory study.

As noted above, the FDA endorses percent patients abstinent during the final weeks of the trial as a primary outcome for efficacy trials for cocaine use disorder. To more closely approximate this outcome measure, we analyzed self-administration data as percent of participants who abstained from cocaine self-administration. A participant was considered abstinent when he/she did not self-administer any cocaine during the experimental sessions in which active doses were tested (i.e., chose all money). The topiramate (100 mg/day)+phentermine (30 mg/day) combination robustly increased the number of participants who abstained from cocaine (40 or 80 mg) self-administration relative to the topiramate (0 mg/day)+phentermine (0 mg/day) condition. Worth mentioning, participants received an initial sampling or "priming" dose of the available intranasal cocaine dose before being allowed to respond to earn the desired proportion that dose later in the session. The administration of cocaine priming doses has previously been shown to impair the ability to avoid initiating cocaine self-administration. These findings suggest that topiramate-phentermine combinations may be especially useful for reducing cocaine relapse. These findings, along with the traditional analysis of the cocaine self-administration data described above, strongly support advancing topiramate-phentermine combinations as a pharmacotherapeutic for cocaine use disorder.

The results of the present human laboratory study suggest the effects of the topiramate-phentermine combinations are larger than those observed with the constituent drugs alone. Both topiramate (100 mg/day) and phentermine (30 mg/day) alone increased the percent of participants who abstained from cocaine self-administration, although not significantly. In contrast, combining these doses produced robust increases in abstinence relative to the topiramate (0 mg/day) and phentermine (0 mg/day) conditions (i.e., 68%). Similar additive effects were observed with the traditional analysis of the self-administration data (i.e., number of drug choices on the progressive-ratio procedure).

CONCLUSIONS

Cocaine use disorder remains an unrelenting public health concern. Despite nearly four decades of research, an effective medication is not yet approved for cocaine use disorder. The results of the present human laboratory study strongly support advancing topiramate-phentermine combinations as a pharmacotherapeutic for treating cocaine use disorder.

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

1. Allison D B, Gadde K M, Garvey W T, Peterson C A, Schwiers M L, Najarian T, Tam P Y, Troupin B, Day W W (2012). Controlled-release phentermine/topiramate in severely obese adults: a randomized controlled trial (EQUIP). Obesity, 20: 330-342.
2. Aragona B J, Cleaveland N A, Stuber G D, Day J J, Carelli R M, Wightman R M (2008). Preferential enhancement of dopamine transmission within the nucleus accumbens shell by cocaine is attributable to a direct increase in phasic dopamine release events. J Neurosci, 28: 8821-8831.
3. Astrup A, Caterson I, Zelissen P, Guy-Grand B, Carruba M, Levy B, Sun X, Fitchet M (2004). Topiramate: long-term maintenance of weight loss induced by a low-calorie diet in obese subjects. Obes Res, 12: 1658-1669. Atkinson R L, Blank R C, Schumacher D, Dhurandhar N V, Ritch D L (1997). Long-term drug treatment of obesity in a private practice setting. Obes Res, 5: 578-586.
4. Baldacara L, Cogo-Moreira H, Parreira B L, Diniz T A, Milhomem J J, Fernandes C C, Lacerda A L (2016). Efficacy of topiramate in the treatment of crack cocaine dependence: a double-blind, randomized, placebo-controlled trial. J Clin Psychiatry, 77: 398-406.
5. Bassareo V, Di Chiara G (1999). Differential responsiveness of dopamine transmission to food-stimuli in nucleus accumbens shell/core compartments. Neuroscience, 89: 637-641.
6. Blumenthal D M, Gold M S (2010). Neurobiology of food addiction. Curr Opin Clin Nutr Metab Care, 13: 359-365.
7. Bolin B L, Lile J A, Marks K R, Beckmann J S, Rush C R, Stoops W W (2016). Buspirone reduces sexual risk-taking intent but not cocaine self-administration. Experimental and Clinical Psychopharmacology, 24: 162-173.
8. Bray G A, Hollander P, Klein S, Kushner R, Levy B, Fitchet M, Perry B H (2003). A 6-month randomized, placebo-controlled, dose-ranging trial of topiramate for weight loss in obesity. Obes Res, 11: 722-733. Center for Disease Control and Prevention (2010). Obesity and Overweight, http://www.cdc.gov/nchs/fastats/over-wt.htm. Accessed Nov. 17, 2010.
9. Centers for Disease Control and Prevention (2018). National Center for Health Statistics. Multiple Cause of Death 1999-2017 on CDC WONDER Online Database. Released December 2018. Accessed Mar. 1, 2019: https://www.drugabuse.gov/related-topics/trends-statistics/overdose-death-rates.
10. Chan B, Kondo K, Freeman M, Ayers C, Montgomery J, Kansagara D (2019). Pharmacotherapy for Cocaine Use Disorder-a Systematic Review and Meta-analysis. J Gen Intern Med 34:2858-2873.
11. Churchill L, Dilts R P, Kalivas P W (1992). Autoradiographic localization of ☐-Aminobutyric acidA receptors within the ventral tegmental area. Neurochem Res, 17: 101-106.

12. Cormr S D, Ashworth J B, Foltin R W, Johanson C E, Zacny J P, Walsh S L (2008). The role of human drug self-administration procedures in the development of medications. Drug Alcohol Depend, 96: 1-15.
13. Covi L, Hess J M, Schroeder J R, Preston K L (2002). A dose response study of cognitive behavioral therapy in cocaine abusers. J Subst Abuse Treat, 23: 191-197.
14. Czoty P W, William W. Stoops W W, Rush C R (2016). Evaluation of the "Pipeline" for Development of Medications for Cocaine Use Disorder: A Review of Translational Animal Laboratory, Human Laboratory and Clinical Trial Research. Pharmacol Rev, 68: 533-562.
15. de Lima M S, de Oliveira Soares B G, Reisser A A, Farrell M (2002). Pharmacological treatment of cocaine dependence: A systematic review. Addiction, 97: 931-949.
16. de Wit H, Clark M, Brauer L H (1997). Effects of d-amphetamine in grouped versus isolated humans. Pharmacol Biochem Behav, 57: 333-340.
17. Dewey S L, Chaurasia C S, Chen C E, Volkow N D, Clarkson F A, Porter S P, Straughter-Moore R M, Alexoff D L, Tedeschi D, Russo, N B, Fowler J S, Brodie J D (1997). GABAergic attenuation of cocaine-induced dopamine release and locomotor. Synapse, 25: 393-398.
18. Donny E C, Bigelow G E, Walsh S L (2004) Assessing the initiation of cocaine self-administration in humans during abstinence: effects of dose, alternative reinforcement, and priming. Psychopharmacology, 172: 316-323.
19. Dutra L, Stathopoulou G, Basden S L, Leyro T M, Powers M B and Otto M W (2008). A meta-analytic review of psychosocial interventions for substance use disorders. Am J Psychiatry, 165: 179-187.
20. Farronato N S, Dursteler-Macfarland K M, Wiesbeck G A and Petitjean S A (2013). A systematic review comparing cognitive-behavioral therapy and contingency management for cocaine dependence. Journal of Addictive Diseases, 32: 274-287.
21. Foltin R W, Haney M (2004) Intranasal cocaine in humans: Acute tolerance, cardiovascular and subjective effects. Pharmacol Biochem Behav, 78:93-101.
22. Finlay J M, Damsma G, Fibiger H C (1992). Benzodiazepine-induce decreases in extracellular concentrations of dopamine in the nucleus accumbens after acute and repeated administrations. Psychopharmacology, 106: 202-208.
23. Gadde K M, Allison D B, Ryan D H, Peterson C A, Troupin B, Schwiers M L, Day W W (2011). Effects of low-dose, controlled-release, phentermine plus topiramate combination on weight and associated comorbidities in overweight and obese adults (CONQUER): a randomised, placebo-controlled, phase 3 trial. Lancet, 377: 1341-1352.
24. Garvey W T, Ryan D H, Look M, Gadde K M, Allison D B, Peterson C A, Schwiers M, Day W W, Bowden C H (2012). Two-year sustained weight loss and metabolic benefits with controlled-release phentermine/topiramate in obese and overweight adults (SEQUEL): a randomized, placebo-controlled, phase 3 extension study. Am J Clin Nutr, 95: 297-308.
25. Glowa J R, Rice K C, Matecka D, Rothman R B (1997) Phentermine/fenfluramine decreases cocaine self-administration in rhesus monkeys. Neuroreport 8:1347-1351.
26. Grabovsky Y, Tallarida R J (2004). Isobolographic analysis for combinations of a full and partial agonist: curved isoboles. J Pharmacol Exp Ther, 310: 981-986.
27. Grabowski J, Rhoades H, Schmitz J, Stotts A, Daruzska L A, Creson D, Moeller F G (2001). Dextroamphetamine for cocaine-dependence treatment: A double-blind randomized clinical trial. J Clin Psychopharmacol, 21: 522-526.
28. Grabowski J, Rhoades H, Stotts A, Cowan K, Kopecky C, Dougherty A, Moeller F G, Hassan S, Schmitz J (2004). Agonist-like or antagonist-like treatment for cocaine dependence with methadone for heroin dependence: Two double-blind randomized clinical trials. Neuropsychopharmacology, 29: 969-81.
29. Rush, Craig Roy Greenwald M K, Lundahl L H, Steinmiller C L (2010). Sustained release d-amphetamine reduces cocaine but not 'speedball'-seeking in buprenorphine-maintained volunteers: a test of dual-agonist pharmacotherapy for cocaine/heroin polydrug abusers. Neuropsychopharmacology, 35: 2624-2637.
30. Guardia D, Rolland B, Karila L, Cottencin O (2011) GABAergic and glutamatergic modulation in binge eating: therapeutic approach. Curr Pharm Des 17:1396-1409.
31. Haddock C K, Poston W S, Dill P L, Foreyt J P, Ericsson M (2002). Pharmacotherapy for obesity: A quantitative analysis of four decades of published randomized clinical trials. Int J Obes Relat Metab Disord, 26: 262-273.
32. Halford J C, Boyland E J, Blundell J E, Kirkham T C, Harrold J A (2010). Pharmacological management of appetite expression in obesity. Nat Rev Endocrinol, 6: 255-269.
33. Haney M, Spealman R (2008). Controversies in translational research: Drug self-administration. Psychopharmacology, 199: 403-419.
34. Hay P J, Claudino A M (2012). Clinical psychopharmacology of eating disorders: a research update. Int J Neuropsychopharmacol, 15: 209-222.
35. Herin D V, Rush C R, Grabowski J (2010). Agonist-like pharmacotherapy for stimulant dependence: Preclinical, human laboratory and clinical trials. Annals NY Acad Sci, 1187: 76-100.
36. Hermanussen M, Tresguerres J A (2003). Does high glutamate intake cause obesity? J Pediatr Endocrinol Metab, 16: 965-968.
37. Hernandez L, Hoebel B G (1988). Food reward and cocaine increase extracellular dopamine in the nucleus accumbens as measured by microdialysis. Life Sci, 42: 1705-1712.
38. Hernandez L, Lee F, Hoebel B G (1987). Simultaneous microdialysis and amphetamine infusion in the nucleus accumbens and striatum of freely moving rats: increase in extracellular dopamine and serotonin. Brain Res Bull, 19: 623-628.
39. Higgins S T, Heil S H, Lussier J P (2004). Clinical implications of reinforcement as a determinant of substance use disorders. Ann Rev Psychol, 55: 431-61.
40. Invernizzi R, Pozzi L, Samanin R (1991). Release of dopamine is reduced by diazepam more in the nucleus accumbens than in the caudate nucleus of conscious rats. Neuropharmacology, 30: 575-578.
41. Jalal H, Buchanich J M, Roberts M S, Balmert L C, Zhang K, Burke D S (2018). Changing dynamics of the drug overdose epidemic in the United States from 1979 through 2016. Science 361.
42. Javaid J I, Fischman M W, Schuster C R, Dekirmenjiian H, Davis J M (1978). Cocaine plasma concentration: Relation to physiological and subjective effects in humans. Science, 202: 227-228.
43. Johnson B A, Ait-Daoud N, Wang X Q, Penberthy J K, Javors M A, Seneviratne C and Liu L (2013b) Topiramate for the treatment of cocaine addiction: a randomized clinical trial. JAMA Psychiatry 70:1338-1346.

44. Johnson B A, Roache J D, Ait-Daoud N, Gunderson E W, Haughey H M, Wang X Q, Liu L (2012). Topiramate's effects on cocaine-induced subjective mood, craving and preference for money over drug taking. Addict Biol (ePub).
45. Johnson R E, Eissenberg T, Stitzer M L, Strain E C, Liebson I A, Bigelow G E (1995). A placebo controlled clinical trial of buprenorphine as a treatment for opioid dependence. Drug alcohol Depend, 40: 17-25.
46. Johnson R E, Jaffe J H, Fudala P J (1992). A controlled trial of buprenorphine treatment for opioid Alcohol. JAMA, 267: 2750-2755.
47. Kalivas P W (2007). Neurobiology of cocaine addiction: implications for new pharmacotherapy. Am J Addict, 16: 71-78.
48. Kalivas P W, Duffy P, Eberhardt H (1990). Modulation of A10 dopamine neurons by □-aminobutyric acid agonists. J Pharmacol Exp Ther, 253: 858-866.
49. Kampman K M, Pettinati H, Lynch K G, Dackis C, Sparkman T, Weigley C, O'Brien C P (2004). A pilot trial of topiramate for the treatment of cocaine dependence. Drug Alcohol Depend, 75: 233-240.
50. Kampman K M, Pettinati H M, Lynch K G, Spratt K, Wierzbicki M R, O'Brien C P (2013). A double-blind, placebo-controlled trial of topiramate for the treatment of comorbid cocaine and alcohol dependence. Drug Alcohol Depend, 133: 94-99.
51. Kang J G, Park C Y, Kang J H, Park Y W, Park S W (2010). Randomized controlled trial to investigate the effects of a newly developed formulation of phentermine diffuse-controlled release for obesity. Diabetes Obes Metab, 12: 876-882.
52. Karila L, Reynaud M, Aubin H J, Rolland B, Guardia D, Cottencin O, Benyamina A (2011). Pharmacological Treatments for Cocaine Dependence: Is there Something New? Curr Pharmaceutical Design, 17: 1359-1368.
53. Kita H, Kitai S T (1988). Glutamate decarboxylase immunoreactive neurons in the rat neostriatum: Their morphological types and populations. Brain Research, 447: 346-352.
54. Kiluk B D, Carroll K M, Duhig A, Falk D E, Kampman K, Lai S, Litten R Z, McCann D J, Montoya I D, Preston K L, Skolnick P, Weisner C, Woody G, Chandler R, Detke M J, Dunn K, Dworkin R H, Fertig J, Gewandter J, Moeller F G, Ramey T, Ryan M, Silverman K and Strain E C (2016) Measures of outcome for stimulant trials: ACTTION recommendations and research agenda. Drug Alcohol Depend, 158: 1-7.
55. Le Foll B, Justinova Z, Wertheim C E, Barnes C, Goldberg S R (2008). Topiramate does not alter nicotine or cocaine discrimination in rats. Behav Pharmacol, 19: 13-20.
56. Levin F R, Mariani J J, Pavlicova M, Choi C J, Mahony A L, Brooks D J, Bisaga A, Dakwar E, Carpenter K M, Naqvi N, Nunes E V and Kampman K (2020) Extended release mixed amphetamine salts and topiramate for cocaine dependence: A randomized clinical replication trial with frequent users. Drug Alcohol Depend 206: 107700.
57. Lile J A, Stoops W W, Glaser P E A, Hays L R, Rush C R (2004a). Acute administration of the GABA reuptake inhibitor tiagabine does not alter the effects of oral cocaine in humans. Drug Alcohol Depend, 76: 81-91.
58. Lile J A, Stoops W W, Allen T S, Glaser P E A, Hays L R, Rush C R (2004b). Baclofen does not alter the reinforcing, subject-rated or cardiovascular effects of intranasal cocaine in humans. Psychopharmacology, 171: 441-449.
59. Mariani J J, Pavlicova M, Bisaga A, Nunes E V, Brooks D J, Levin F R (2012). Extended-release mixed amphetamine salts and topiramate for cocaine dependence: a randomized controlled trial. Biol Psychiatry 72: 950-956.
60. Mello N K, Mendelson J H (1980). Buprenorphine suppresses heroin use by heroin addicts. Science, 207: 657-659.
61. McKee S A, Carroll K M, Sinha R, Robinson J E, Nich C, Cavallo D, O'Malley S (2007). Enhancing brief cognitive-behavioral therapy with motivational enhancement techniques in cocaine users. Drug Alcohol Depend, 91: 97-101.
62. Mello N K, Mendelson J H, Kuehnle J C (1982). Buprenorphine effects on human heroin self-administration: an operant analysis. J Pharmacol Exp Ther, 223: 30-39Nolan et al., 2019.
63. McNamara J O (2006). Pharmacotherapies of the Epilepsies. In: Brunton L L, Lazo J S, Parker K L (eds), Goodman and Gilman's: The Pharmacological Basis of Therapeutics, Eleventh Edition. New York; McGraw-Hill, pp. 501-525.
64. Morgan A E, Dewey S L (1998). Effects of pharmacologic increase in brain GABA levels on cocaine-induced changes in extracellular dopamine. Synapse, 28: 60-65.
65. Morton G J, Cummings D E, Baskin D G, Barsh G S, Schwartz M W (2006). Central nervous system control of food intake and body weight. Nature, 443: 289-295.
66. Negus S S (2003). Rapid assessment of choice between cocaine and food in rhesus monkeys: effects of environmental manipulations and treatment with d-amphetamine and flupenthixol. Neuropsychopharmacology, 28: 919-931.
67. Ogden C L, Carroll M D, Kit B K, MD, MPH1,2; Katherine M. Flegal K M (2014) Prevalence of Childhood and Adult Obesity in the United States, 2011-2012. JAMA, 311: 806-814.
68. Oliveto A H, Bickel W K, Hughes J R, Shea P J, Higgins S T, Fenwick J W (1992). Caffeine drug discrimination in humans: acquisition, specificity and correlation with self-reports. J Pharmacol Exp Ther 261: 885-894.
69. Rapaka R, Schnur P, Shurtleff D (2008). Obesity and addiction: common neurological mechanisms and drug development. Physiol Behav, 95: 2-9.
70. Redmon J B, Raatz S K, Kwong C A, Swanson J E, Thomas W, Bantle J P (1999). Pharmacologic induction of weight loss to treat type 2 diabetes. Diabetes Care, 22: 896-903.
71. Reiner D J, Bossert J M (2018). Can anti-obesity drugs be repurposed to treat cocaine addiction? Neuropsychopharmacol, 43: 1983-1984.
72. Rothman R B (2010). Treatment of obesity with "combination" pharmacotherapy. Am J Ther, 17: 596-603.
73. Rothman R B, Gendron T, Hitzig P (1994). Letter to the editor. J Substance Abuse Treat, 11: 273-275.
74. Rush C R, Mariani J J, Pavlicova M, Bisaga A, Nunes E V, Brooks D J, Levin F R (2012). Extended-release mixed amphetamine salts and topiramate for cocaine dependence: a randomized controlled trial. Biol Psychiatry 72: 950-956.
75. Rush C R, Stoops W W (2012). Agonist replacement therapy for cocaine dependence: A translational review. Future Medicinal Chemistry, 4: 245-265.

76. Rush C R, Stoops W W, Hays L R, Glaser P E A, Hays L S (2003) Risperidone attenuates the discriminative-stimulus effects of d-amphetamine in humans. J Pharmacol Exp Ther 306:195-204.
77. Rush C R, Stoops W W, Hays L R (2009). Cocaine effects during d-amphetamine maintenance: A human laboratory analysis of safety, tolerability and efficacy. Drug and Alcohol Dependence, 99: 261-271.
78. Rush C R, Stoops W W, Sevak R J, Hays L R (2010). Cocaine choice in humans during d-amphetamine maintenance. J Clin Psychopharmacol, 30: 152-159.
79. Seiden L S, Sabol K E, Ricaurte G A (1993). Amphetamine: effects on catecholamine systems and behavior. Ann Rev Pharmacol Toxicol, 33: 639-677.
80. Sevak R J, Stoops W W, Glaser P E A, Hays L R, Rush C R (2010). Reinforcing effects of d-amphetamine: Influence of novel ratios on a progressive ratio schedule. Behavioural Pharmacology, 21: 745-753.
81. Shiels M S, Freedman N D, Thomas D and Berrington de Gonzalez A (2018). Trends in U.S. Drug Overdose Deaths in Non-Hispanic Black, Hispanic, and Non-Hispanic White Persons, 2000-2015. Ann Intern Med, 168: 453-455.
82. Singh M, Keer D, Klimas J, Wood E, Werb D (2016). Topiramate for cocaine dependence: A systematic review and meta-analysis of randomized controlled trials. Addiction, 111: 1337-1346.
83. Stafford D, LeSage M G, Glowa J R (1999). Effects of phentermine on responding maintained by progressive-ratio schedules of cocaine and food delivery in rhesus monkeys. Behav Pharmacol, 10: 775-784.
84. Stanley M D, Poole M M, Stoops W W, Rush C R (2011). Amphetamine self-administration in light and moderate drinkers. Alcohol Clin Exp Res, 35: 443-453.
85. Stenlof K, Rossner S, Vercruysse F, Kumar A, Fitchet M, Sjostrom L (2007). Topiramate in the treatment of obese subjects with drug-naive type 2 diabetes. Diabetes Obes Metab, 9: 360-368.
86. Stoops W W, Fillmore M T, Poonacha M F, Kingery J E, Rush C R (2003). Alcohol choice and amphetamine effects in light and moderate drinkers. Alcohol Clin Exp Res, 27: 804-811.
87. Stoops W W, Blackburn J W, Hudson D A, Hays L R, Rush C R (2008). Safety, tolerability and subject-rated effects of intranasal cocaine during atomoxetine maintenance. Drug and Alcohol Dependence, 92: 282-285.
88. Stoops W W, Lile J A, Glaser P E A, Hays L R, Rush C R. (2012). Alternative reinforcer response cost impacts cocaine choice in humans. Prog Neuropsychopharmacol Biol Psychiatry, 36: 189-193.
89. Stoops W W, Lile J A, Hays L R, Rush C R (2012). Acute bupropion pretreatment attenuates the reinforcing effects of intranasal cocaine. Addiction, 107: 1140-1147.
90. Stoops W W, Lile J A, Rush C R (2010). Monetary alternative reinforcers more effectively decrease intranasal cocaine choice than food alternative reinforcers. Pharmacol Biochem Behav, 95: 187-191.
91. Stoops W W, Rush C R (2013). Agonist Replacement for Stimulant Dependence: A Review of Clinical Research. Curr Pharmaceutical Design, in press.
92. Stoops W W, Rush C R (2014). Combination pharmacotherapies for stimulant use disorder: a review of clinical findings and recommendations for future research. Expert Rev Clin Pharmacol, 7: 363-374.
93. Stoops W W, Strickland J C, Hays L R, Rayapati A O, Lile J A, Rush, C. R. (2016). Safety and tolerability of intranasal cocaine during phendimetrazine maintenance. Psychopharmacology, 233: 2055-2063. Tomasi D, Volkow ND (2013). Striatocortical pathway dysfunction in addiction and obesity: differences and similarities. Crit Rev Biochem Mol Biol, 48: 1-19.
94. Stout R L, Wirtz P W, Carbonari J P, Del Boca F K (1994). Ensuring balanced distribution of prognostic factors in treatment outcome research. J Studies Alc (Suppl 12): 70-75.
95. Substance Abuse and Mental Health Services Administration (2013a). Treatment Episode Data Set (TEDS) Highlights—2009 National Admissions to Substance Abuse Treatment Services. Office of Applied Studies: Rockville, Md., USA. http://www.dasis.samhsa.gov/webt/quicklink/US09.htm. Accessed 28 Jan. 2013.
96. Substance Abuse and Mental Health Services Administration (2013b). Results from the 2010 National Survey on Drug Use and Health: National Findings. Office of Applied Studies: Rockville, Md., USA. http://www.dasis.samhsa.gov/webt/quicklink/US10.htm. Accessed 28 Jan. 2013.
97. Substance Abuse and Mental Health Services Administration (2012). Results from the 2011 National Survey on Drug Use and Health: National Findings. Office of Applied Studies: Rockville, Md., USA. http://http://www.samhsa.gov/data/NSDUH/2k10NSDUH/2k10Results.htm. Accessed 28 Jan. 2013.
98. Tallarida R J (2006). An overview of drug combination analysis with isobolograms. J Pharmacol Exp Ther, 319: 1-7.
99. Tomasi D, Wang G J, Wang R, Caparelli E C, Logan J, Volkow N D (2015). Overlapping patterns of brain activation to food and cocaine cues in cocaine abusers: association to striatal D2/D3 receptors. Hum Brain Mapp, 36: 120-136.
100. Torregrossa M M, Kalivas P W (2008). Microdialysis and the neurochemistry of addiction. Pharmacol Biochem Behav, 90: 261-272.
101. Trinko R, Sears R M, Guarnieri D J, DiLeone R J (2007). Neural mechanisms underlying obesity and drug addiction. Physiol Behav, 91: 499-505.
102. Vansickel A R, Stoops W W, Rush C R (2010). Human sex differences in d-amphetamine self-administration. Addiction, 105: 727-731.
103. Vocci F J, Elkashef A (2005). Pharmacotherapy and other treatments for cocaine abuse and dependence. Curr Opin Psychiatry, 18: 265-270.
104. Vocci F J, Montoya I D (2009). Psychological treatments for stimulant misuse, comparing and contrasting those for amphetamine dependence and those for cocaine dependence. Curr Opin Psychiatry, 22: 263-268. Volkow N D, Fowler J S (2000). Addiction, a disease of compulsion and drive: involvement of the orbitofrontal cortex. Cereb Cortex, 10: 318-325.
105. Volkow N D, Baler R D (2015). NOW vs LATER brain circuits: implications for obesity and addiction. Trends Neurosci, 38:345-352.
106. Volkow N D, Fowler J S, Wang G J, Hitzemann R, Logan J, Schlyer D J, Dewey S L, Wolf A P (1993). Decreased dopamine D2 receptor availability is associated with reduced frontal metabolism in cocaine abusers. Synapse, 14: 169-177.
107. Volkow N D, Fowler J S, Wolf A P, Schlyer D, Shiue C Y, Alpert R et al. (1990). Effects of chronic cocaine abuse on postsynaptic dopamine receptors. Am J Psychiatry, 147: 719-724.
108. Volkow N D, Wang G J, Telang F, Fowler J S, Thanos P K, Logan J, et al. (2008). Low dopamine striatal D2 receptors are associated with prefrontal metabolism in obese subjects: Possible contributing factors. Neuroimage, 42: 1537-1543.

109. Volkow N D, Wang G J, Tomasi D, Baler R D (2013). The addictive dimensionality of obesity. Biol Psychiatry, ePub.
110. Volkow N D, Wise R A (2005). How can drug addiction help us understand obesity? Nat Neurosci, 8: 555-560. Wang G J, Volkow N D, Logan J, Pappas N R, Wong C T, Zhu W et al. (2001). Brain dopamine and obesity. Lancet, 357: 354-357.
111. Wang G J, Volkow N D, Thanos P K, Fowler J S (2004). Similarity between obesity and drug addiction as assessed by neurofunctional imaging: A concept review. J Addict Dis, 23: 39-53.
112. Weintraub M (1992). Long-term weight control: the National Heart, Lung, and Blood Institute funded multimodal intervention study. Clin Pharmacol Ther, 51: 581-585.
113. Wessinger W (1986). Approaches to the study of drug interactions in behavioral pharmacology. Neurosci Biobehav Rev, 10: 103-113.
114. Westfall T C, Westfall D P (2006). Adrenergic agonist and antagonists. In: Brunton L L, Lazo J S, Parker K L (eds), Goodman and Gilman's: The Pharmacological Basis of Therapeutics, Eleventh Edition. New York; McGraw-Hill, pp. 217-236.
115. Wilding J, Van Gaal L, Rissanen A, Vercruysse F, Fitchet M (2004). A randomized double-blind placebo-controlled study of the long-term efficacy and safety of topiramate in the treatment of obese subjects. Int J Obes Relat Metab Disord, 28: 1399-1410.
116. Winchell C, Rappaport B A, Roca R, Rosebraugh C J (2012). Reanalysis of methamphetamine dependence treatment trial. CNS Neurosci Ther, 18: 367-368.
117. Wojnicki F H, Rothman R B, Rice K C, Glowa J R (1999). Effects of phentermine on responding maintained under multiple fixed-ratio schedules of food and cocaine presentation in the rhesus monkey. J Pharmacol Exp Ther, 288: 550-560.
118. Woolverton W L (1987). Analysis of drug interactions in behavioral pharmacology. In Neurobehavioral Pharmacology [Vol. 6]. (eds) T. Thompson, P. B. Dews and J. E. Barrett. Lawrence Erlbaum Assoc., Inc., Hillsdale, N.J., pp. 275-302.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A method of treating a subject who is experiencing or is at risk of experiencing an undesired consequence of cocaine use, the method comprising administering a combination of topiramate in a dose of 50 mg/day to 100 mg/day and phentermine in a dose of 15 mg/day to 30 mg/day to the subject.

2. The method of claim 1, wherein the undesired consequence of cocaine use is craving for administration of a stimulant.

3. The method of claim 2, wherein the stimulant is cocaine.

4. The method of claim 1, wherein cocaine use includes cocaine misuse.

5. The method of claim 4, wherein the subject is diagnosed with stimulant use disorder.

6. The method of claim 5, wherein the subject is diagnosed with cocaine use disorder.

7. The method of claim 1, wherein administering the combination includes administering the topiramate in a dose of more than 50 mg/day.

8. The method of claim 1, wherein administering the combination includes administering the topiramate in a dose of 100 mg/day.

9. The method of claim 1, wherein administering the combination includes administering the phentermine in a dose of more than 15 mg/day.

10. The method of claim 1, wherein administering the combination includes administering the phentermine in a dose of 30 mg/day.

11. The method of claim 1, wherein administering the combination includes administering the topiramate in a dose of 100 mg/day and administering the phentermine in a dose of 30 mg/day.

12. The method of claim 1, wherein administering the combination comprises administering the combination as a composition that includes both the topiramate and the phentermine.

13. A method for treating cocaine use disorder, the method comprising administering an effective dose of a combination of topiramate in a dose of 50 mg/day to 100 mg/day and phentermine in a dose of 15 mg/day to 30 mg/day to a subject with cocaine use disorder.

14. The method of claim 13, wherein administering the combination includes administering the topiramate in a dose of more than 50 mg/day.

15. The method of claim 13, wherein administering the combination includes administering the phentermine in a dose of more than 15 mg/day.

16. The method of claim 13, wherein administering the combination includes administering the phentermine in a dose of 30 mg/day.

17. The method of claim 13, wherein administering the combination includes administering the topiramate in a dose of 100 mg/day and administering the phentermine in a dose of 30 mg/day.

18. The method of claim 13, wherein administering the combination includes administering topiramate in a dose of 100 mg/day.

* * * * *